(12) United States Patent
Sabaawy et al.

(10) Patent No.: US 11,565,264 B2
(45) Date of Patent: Jan. 31, 2023

(54) EXPANDABLE ARRAYS AND METHODS OF USE

(71) Applicant: Rutgers, The State University of New Jersey, New Brunswick, NJ (US)

(72) Inventors: Hatem E. Sabaawy, New Brunswick, NJ (US); Howon Lee, Piscataway, NJ (US); Chen Yang, New Brunswick, NJ (US); Daehoon Han, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 158 days.

(21) Appl. No.: 17/085,985

(22) Filed: Oct. 30, 2020

(65) Prior Publication Data
US 2021/0162408 A1    Jun. 3, 2021

Related U.S. Application Data

(63) Continuation-in-part of application No. PCT/US2019/029931, filed on Apr. 30, 2019.

(60) Provisional application No. 62/664,740, filed on Apr. 30, 2018.

(51) Int. Cl.
*B01L 3/00*    (2006.01)

(52) U.S. Cl.
CPC ... *B01L 3/50855* (2013.01); *B01L 2300/0636* (2013.01); *B01L 2300/18* (2013.01)

(58) Field of Classification Search
CPC ......... B01L 3/50855; B01L 2300/0636; B01L 2300/18; B01L 2300/0829; B01L 2300/123; C12M 23/12; C12M 23/26
See application file for complete search history.

(56) References Cited

U.S. PATENT DOCUMENTS

| 7,654,595 B2 | 2/2010 | Yokoyama et al. |
| 9,339,950 B2 | 5/2016 | Allen |
| 2011/0257459 A1 | 10/2011 | Sutton et al. |

(Continued)

FOREIGN PATENT DOCUMENTS

| WO | WO 2012/107241 A2 | 8/2012 |
| WO | 2016187614 A1 | 11/2016 |
| WO | 2019213093 A1 | 11/2019 |

OTHER PUBLICATIONS

International Search Report and Written Opinion for Int'l Application No. PCT/US2019/029931, titled: Expandable Arrays and Methods of Use, dated Jul. 17, 2019.

(Continued)

*Primary Examiner* — Christopher Adam Hixson
(74) *Attorney, Agent, or Firm* — Hamilton, Brook, Smith & Reynolds, P.C.

(57) ABSTRACT

An expandable array and methods of maintaining a biological sample within an expandable array are provided. The expandable array includes a plurality of receptacles configured to receive a biological sample and a plurality of beams comprising a programmable material. Each beam of the plurality of beams is located between and connects at least two receptacles. The programmable material can be a shape-memory polymer or a magnetoactive material that transitions the plurality of beams from an extended state to a contracted state upon application of a stimulus.

24 Claims, 35 Drawing Sheets
(33 of 35 Drawing Sheet(s) Filed in Color)

(56) References Cited

U.S. PATENT DOCUMENTS

2018/0071731 A1    3/2018   Ho

OTHER PUBLICATIONS

International Preliminary Report on Patentability for Int'l Application No. PCT/US2019/029931, titled: Expandable Arrays and Methods of Use, dated Nov. 3, 2020.
Chadwick, M. et al., "Rapid Processing and Drug Evaluation in Glioblastoma Patient-Derived Organoid Models with 4D Bioprinted Arrays," iScience, vol. 23; 32 pages (2020).
Kim. Y. et al., "Printing ferromagnetic domains for untethered fast-transforming soft materials," Nature, vol. 558; 274-279 (2018).
Yang, C. et al., "4D-Printed Transformable Tube Array for High-Throughput 3D Cell Culture and Histology," Adv. Matter, 2004285; 7 pages (2020).

EXPANDABLE ARRAYS AND METHODS OF USE

RELATED APPLICATION

This application is a continuation-in-part application of International App. No. PCT/US2019/029931, filed on Apr. 30, 2019, which claims the benefit of U.S. Provisional Application No. 62/664,740, filed on Apr. 30, 2018. The entire teachings of the above applications are incorporated herein by reference.

GOVERNMENT SUPPORT

This invention was made with government support under Grant Nos. 5R01CA226746 and P30CA072720, awarded by the National Cancer Institute, and Grant No. 18x092, awarded by the National Institutes of Health. The government has certain rights in the invention.

BACKGROUND 3D printing (3DP) is a class of processes where successive layers of material are aggregated incrementally to directly form a three-dimensional (3D) object [1]. Several 3DP techniques have been introduced over the past several decades [1,2]. While individual processes differ depending on the material and machine technology used, the 3DP processes that use a lithographic technique using a digital light processing (DLP) technology have made great progress in the past several years [3-5].

Projection micro-stereolithography (PμSL) is a micro additive manufacturing technique based on DLP that has been developed and that can provide for high-resolution, rapid, and scalable printing of 3D objects. PμSL uses a spatial light modulator, typically a digital micro-mirror device (DMD), as a dynamically reconfigurable digital photomask. PμSL is capable of fabricating complex 3D microstructures in a bottom-up, layer-by-layer fashion.

SUMMARY

Expandable arrays that can be manufactured by 3DP techniques, including, for example, by PμSL, and methods of maintaining biological samples in such expandable arrays are provided. The arrays can provide for the streamlined processing of biological samples from collection and/or cell culturing to histological analysis.

An expandable array includes a plurality of receptacles configured to receive a biological sample and a plurality of beams comprising a shape-memory polymer. Each beam of the plurality of beams is disposed to extend between and connect at least two receptacles.

The receptacles of the array can also comprise a shape-memory polymer. The shape-memory polymer can be a thermally responsive polymer, for example, a polymer having a transition temperature of greater than about 37° C. and less than about 80° C., or greater than about 37° C. and less than about 50° C. The shape-memory polymer can be an acrylate-based polymer or methacrylate-based polymer. Examples of suitable shape-memory polymers include polyacrylic acid, polyethylene glycol diacrylate, polyethylene glycol dimethacrylate, diethylene glycol dimethacrylate, bisphenol A ethoxylate dimethacrylate, tert-butyl acrylate, and n-Butyl methacrylate. The shape-memory polymer can be compatible with PμSL printing methods.

The beams, or at least a subset of the beams, can be of an expandable shape, including, for example, a serpentine shape, a corrugated shape, a pleated shape, a helical shape, or a folded shape. The beams can be disposed to extend between sides of the receptacles, to extend from a top edge of the receptacles, to extend from a bottom edge, or any combination thereof. Each beam of the plurality of beams can be configured to be disposed in an extended state and a contracted state. A distance between each of the receptacles can be about 2 to about 10 times greater, or about 4 to about 5 times greater, when each beam is in the expanded state than the contracted state. The beams can be configured to revert to the contracted state from the extended state at a transition temperature of the shape memory polymer. Each of the receptacles can be connected to each neighboring receptacle by at least one beam.

The expandable array can be configured to fit within a histology cassette when the beams are in the contracted state. For example, the array can have a width of about 20 mm to about 30 mm and a length of about 25 mm to about 35 mm when each beam is in the contracted state. In a particular example, the array can have a width of about 24 mm and a length of about 30 mm when each beam is in the contracted state. The expandable array can be further configured to be received by a multiwell plate, such as a 96-well, 24-well, or 6-well plate, when the beams are in the expanded state. For example, the plurality of receptacles can be arranged in an 8×12, 4×6, or 2×3 array.

The array can further include at least one handle located at its perimeter, such as to provide for easy handling of the array during transport of the array from a multiwell plate to a histology cassette. If at least two handles are included in the array, each handle can be located at an opposing side of a perimeter of the array. Each handle can be connected to at least two receptacles, although the handles may be connected to multiple receptacles, for example, to provide for more secure handling of larger arrays.

Each receptacle can comprise a mesh structure, such as a mesh structure configured to retain a biological sample. The mesh structure can have a pore size of about 2 μm to about 10 μm. The dimensions of each receptacle can vary. Each receptacle can have a diameter configured to interface with or fit within a diameter of a well. The diameter of each receptacle can be, for example, of about 0.5 mm to about 2.5 mm, of about 0.5 mm to about 1.5 mm, or of about 1 mm. Similarly, each receptacle can have a depth configured to interface with or fit within a well. Each receptacle can have, for example, a depth of about 2 mm to about 15 mm, of about 5 mm to about 15 mm, of about 3 mm to about 5 mm, or of about 11 mm. A height of a combined receptacle and connecting beam(s) can be of about 5 mm to about 15 mm in a contracted state. The wall thickness of each receptacle can be of about 50 μm to about 150 μm, or of about 100 μm.

A method of maintaining a biological sample includes placing an expandable array in a multiwell plate and placing a biological sample within at least a subset of the plurality of receptacles of the array. The method further includes removing the expandable array containing the biological sample from the multiwell plate and exposing the expandable array to a stimulus. The plurality of beams of the expandable array responsively transition to a contracted state, with the biological sample being maintained within the array during the transition.

The exposure of the expandable array to a stimulus can include exposure to a temperature change, for example, an increase in temperature, such as provided by a heat source. The method can further include transferring the expandable array containing the biological sample to a histology cassette. During transfer, a relative configuration of the receptacles can be maintained and the biological sample can be maintained within the respective receptacles (e.g., in a same or similar orientation).

The placement of a biological sample within the receptacle(s) of the array can include seeding a cell culture within at least a subset of the receptacles. The biological sample can be, for example, cells, simple spheroids, mixed spheroids, or organoids. Alternatively, the biological sample can be a tissue specimen.

A kit includes an expandable array, one or more biomolecules and a cell culture medium or the ingredients for making a cell culture medium. The biomolecules can be, for example, a growth factor and/or an extracellular matrix component.

An expandable array, as described above, can include other types of programmable materials, instead of or in addition to shape-memory polymers. The programmable material can be configured to transition each beam from an expanded state to a contracted state upon application of a stimulus.

The programmable material can be a magnetoactive material, and the stimulus can be a magnetic field. The magnetoactive material can comprise a polymer material, such as an elastomer, within which magnetic or magnetizable particles are disposed. The magnetic or magnetizable particles can comprise a ferromagnetic or ferrimagnetic material. For example, the magnetizable particles can be particles of neodymium iron boron.

Each beam can include two or more sections of magnetoactive material having opposite magnetic orientation, so as to provide for a folding of the beam upon application of a magnetic field. The beam can be configured to fold at a transition between the at least two sections. Other beam arrangements can be as described above. The receptacles and overall configuration of the expandable array can include features as described above.

Methods of maintaining a biological sample, as described above, can include exposing the expandable array to a stimulus that is a magnetic field.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Figure 1:
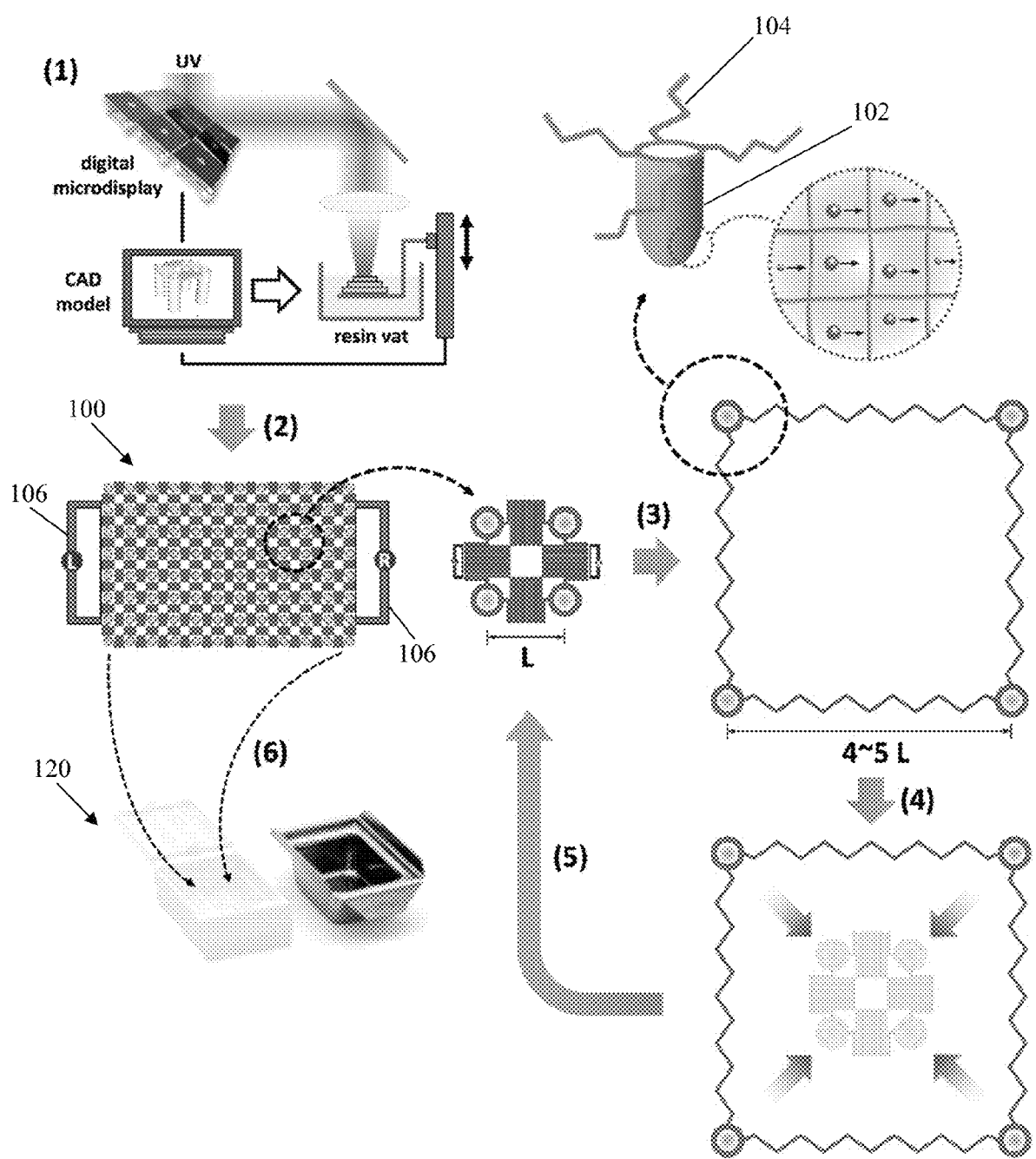
FIG. 1 is a schematic of an expandable array and methods of making and using same.

As shown in FIG. 1, expandable arrays comprising a shape-memory polymer can be made using 3D printing techniques, including PμSL techniques. In an expanded state, the receptacles of the expandable array can be configured to interface with, or fit within a multiwell plate. The array can be configured such that, upon exposure to a stimulus, the shape-memory polymer reverts to a contracted state that can fit within a container of a different dimension, such as a histology cassette, as will be described further below.

PμSL is capable of fabricating complex 3D micro-structures in a bottom-up, layer-by-layer fashion. Generally, PμSL techniques involve the following steps. A digital model created by computer-aided-design (CAD) software is first sliced into a series of closely spaced horizontal planes. These two-dimensional slices are digitized as an image and transmitted to a dynamic mask, which projects the image through a reduction lens into a bath of photosensitive polymer resin. The exposed material cures, and the stage on which it rests is lowered to repeat the process with the next image slice. A schematic representation of this process is shown in FIG. 1 at section (a).

PμSL processes can rapidly generate complex 3D geometries, for example, within minutes, with photo-curable polymers. The high resolution (<5 μm) offered by PμSL is at least an order of magnitude better than most 3DP techniques. Scalability is another prominent attribute of PμSL over other existing 3D printing techniques. Unlike other widely used 3DP processes where a time-consuming raster scanning of a laser beam or an injection nozzle must be performed for each single layer (a serial process), PμSL solidifies the entire layer with a single illumination of ultra-violet (UV) light within a few seconds (a parallel process). Therefore, fabrication of a complex 3D structure could be completed within an hour, compared to the lengthy processing time of several hours to days for other 3D printing methods. Also, by adopting step-and-repeat process, the build-area of PμSL can be extended to a larger area without compromising resolution.

Furthermore, being able to modulate UV light intensity digitally and individually at a single pixel level, PμSL provides for the flexibility to generate the desired material properties and refine their spatial distribution. The intensity of the light exposure strongly influences the crosslinking density of photo-polymerized material, which is an important factor in determining and adjusting physical properties of a polymer, such as elastic modulus, molecular permeability and swelling ratio. Molecular diffusivity of the polymer can be adjusted to provide for receptacles that allow for culture medium and growth factors to diffuse across the receptacle wall.

Smart materials are materials that can actively deform and reconfigure when exposed to external stimuli. 3D printing of shape-shifting materials, such as stimuli-responsive hydrogels and shape memory polymers, has been explored and is termed 4D printing, with the 4th dimension being the time-dependent shape change of 3D printed objects in response to an environmental stimulus [6-8].

4D printing of programmable smart material can be used to generate receptacles, and arrays of receptacles, for use in processing biological samples, such as 3D cultures involving cellular spheres and organoids, or tissue samples. Typically, such biological samples are cultured in multi-well plates. Following culturing, or tissue collection, the samples are transferred to a histology cassette for further analysis by microscopy techniques. The transfer of the biological samples from multiwell plates to a histology cassette is time intensive and manually detailed, often taking about four days and requiring multiple steps to preserve the relative orientation of the samples.

Expandable arrays are described that can interface with or fit within multiwell plates, or other cell-culturing/tissue-collection vessels, and can advantageously provide for streamlined transport of biological samples from the multi-well plates to containers of a different dimension, such as histology cassettes, upon completion of cell-culturing or tissue collection. For example, an expandable array can be configured to transition from a larger footprint (e.g., a 96-well plate) to a smaller footprint (e.g., a paraffin embedding block), while retaining the biological sample(s) in a relative orientation.

As used herein, the term "array" applies to any configuration of two or more receptacles for receiving a biological sample, with at least a subset of the receptacles connected to one another by a beam. For example, the array can be a regularly shaped or patterned array, such as an 8×12 array configured to interface with a 96-well plate, or an irregularly shaped or patterned array, such as an array of 3 receptacles arranged in a triangle or 7 receptacles arranged in a circle.

The term "beam," as used herein, applies to any connecting element extending between receptacles of an array. Beams can extend between upper, lower, and side surfaces of receptacles, in any combination. For example, a beam can be a corrugated or serpentine connecting element extending between sides of receptacles. A beam can also be a helical connecting element that extends from an upper surface of a receptacle. Beams may be integral with the receptacles of an array, integral with other beams, or integral with both receptacles and other beams. Alternatively, beams can be coupled to receptacles and/or to other beams, such as through bonding. Beams may alternatively be referred to as bridges.

As used herein, the term "receptacle" applies to any structure configured to retain a volume of a fluid or solid, including, for example, cells, cell culture media, and tissue samples. Receptacles may be alternatively referred to as baskets.

An example of an expandable array 100, including a method of making and using an expandable array, is shown in FIG. 1. As illustrated, the array 100 is an 8×12 3D cell culture array, which, as printed by PµSL, has a dimension that fits a paraffin embedding cassette 120 (e.g., 24 m×30 m×11 mm). See (1), (2), and (6) of FIG. 1. The array 100 includes a plurality of receptacles 102, illustrated as baskets, each basket having a dimension allowing it to fit within a well of a 96-well plate (e.g., a diameter of 1 mm, a wall thickness of 100 µm, and a U-shaped bottom). See (3) of FIG. 1. Each basket is connected to neighboring baskets with a beam 104, alternatively referred to as a bridge, such as a corrugated or serpentine beam. When the beams 104 are stretched, a center-to-center distance between the baskets matches that of the wells of a multiwell plate, such as the standard 96-well plate illustrated in FIG. 1. In particular, as illustrated, a conversation ratio between the dimensions of the two states (e.g., a contracted/printed state and an expanded state) can be about 1:4-5 and can be provided by 4D printing. See (3), (4), and (5) of FIG. 1.

As illustrated, the array is printed in the contracted, or shrunken, configuration (as shown in steps (1)-(3) of FIG. 1) with an original dimension that matches that of an interior of a paraffin-embedding cassette. After printing, the array is mechanically and bidirectionally stretched to the expanded, or extended, configuration with a dimension that is about 4-5 times that of the original dimension and matching that of a standard 96 well plate (as shown in step (3) of FIG. 1). Optionally, the array can include handles, such as right and left handles 106, for ease of manipulation and assistance in maintaining a correct orientation. While a rectangular array is depicted in FIG. 1 with the handles 106 disposed at opposing ends of the array of receptacles, handles may be positioned at orientation for both regularly and irregularly patterned arrays. The handles can be connected to the receptacles 102, to the beams 104, or to both the receptacles and the beams.

Since the basket array is printed with shape memory polymer, its stretched dimension can be temporarily fixed in the extended configuration. In the extended configuration, the array can be transferred to a standard 96 well plate for 3D cell culturing processes. During the cell culture period, the extended dimension can be retained by itself without any additional aid. PµSL printing advantageously provides for a tunable molecular diffusivity of the basket such that the basket can allow for material exchange while the cell culture is retained inside each basket. Once cell culturing is completed, the culture can then be subjected to formalin fixation and, optionally, the plate can be subjected to brief centrifugation to cause the spheres or organoids to lie at a same level at the bottom of the baskets. The rounded bottom of the baskets can help to maintain the shape of the spheres and organoids during processing.

The entire array can be taken out of the 96 well plate and placed in an incubator, or exposed to a temperature change. In the case of a thermally responsive shape-memory polymer, the temperature can be gradually increased to above the glass transition temperature of the shape memory polymer, upon which the basket array will return to its shrunken configuration. See (4) and (5) of FIG. 1.

Figure 2A:
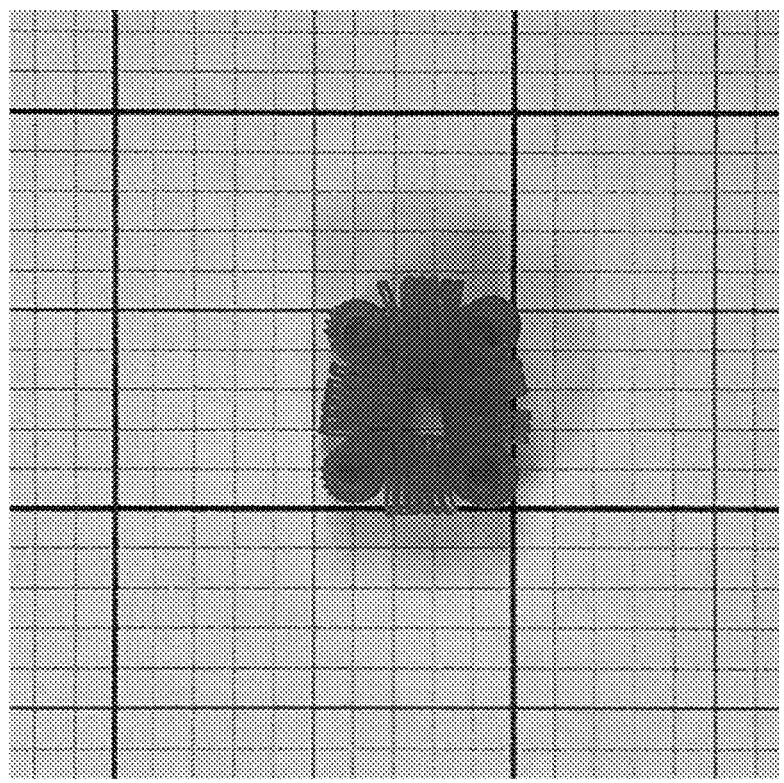
FIG. 2A is a top view of an expandable array in a contracted state. Small grid lines are 2 mm and large grid lines are 10 mm.
Figure 2B:
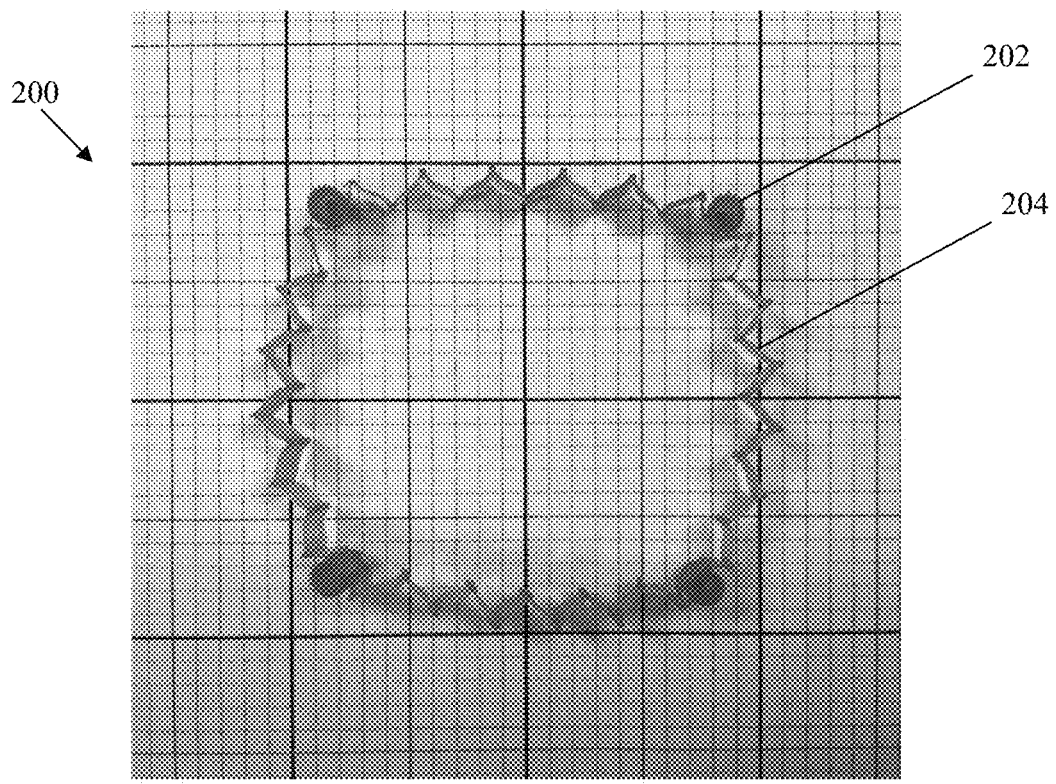
FIG. 2B is a top view of the expandable array of FIG. 2A in an expanded state. Small grid lines are 2 mm and large grid lines are 10 mm.
Figure 2C:
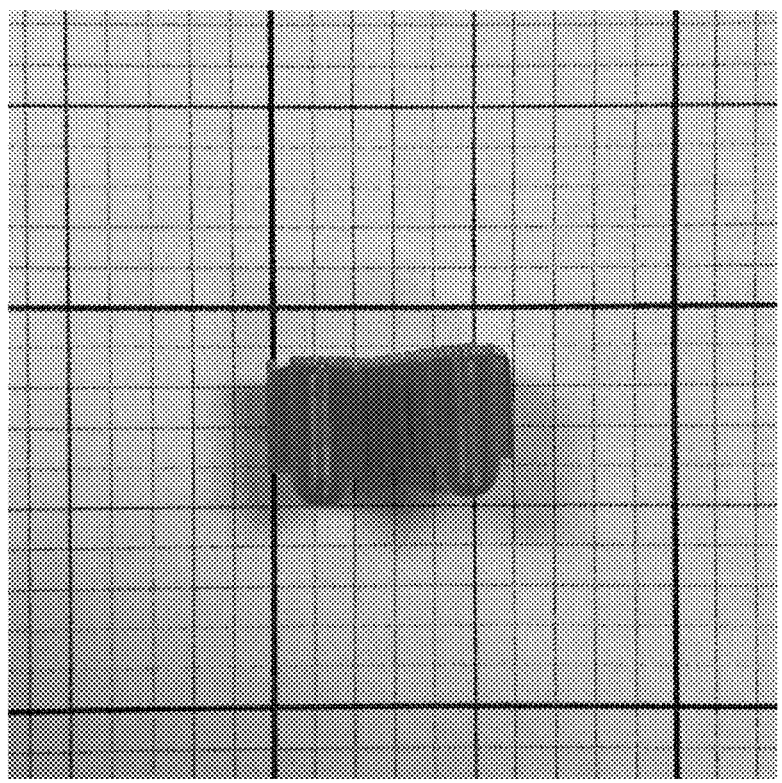
FIG. 2C is a side view of the expandable array of FIG. 2A. Small grid lines are 2 mm and large grid lines are 10 mm.
Figure 3A:
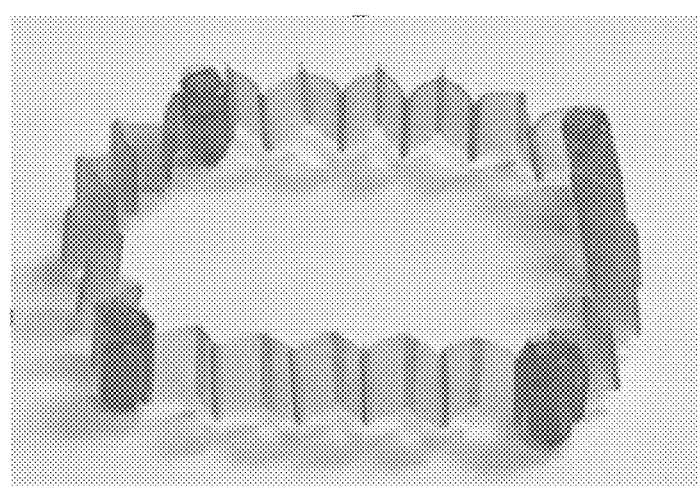
FIG. 3A is perspective view of an expandable array in a substantially expanded state.
Figure 3B:
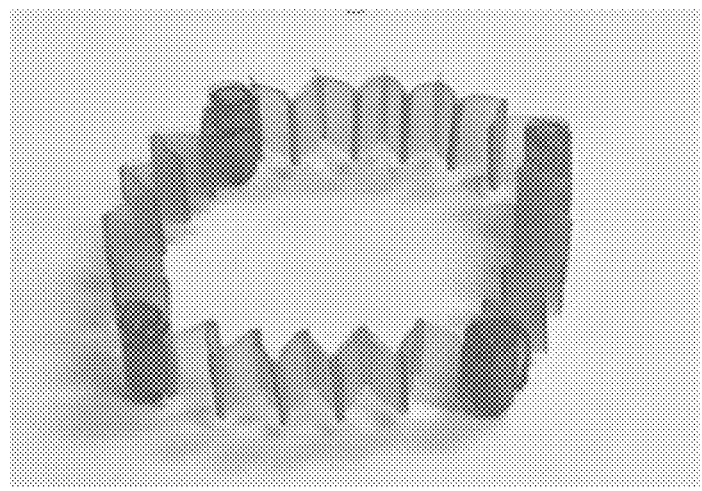
FIG. 3B is a perspective view of the expandable array of FIG. 3A during contraction.
Figure 3C:
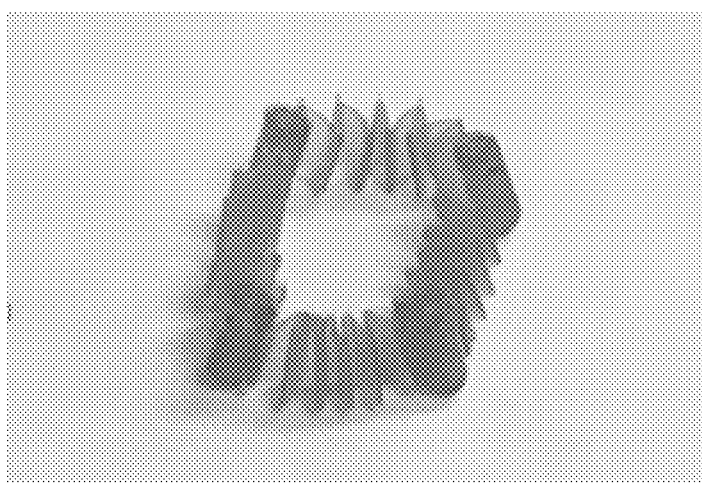
FIG. 3C is a perspective view of the expandable array of FIG. 3A after having further contracted.
Figure 3D:
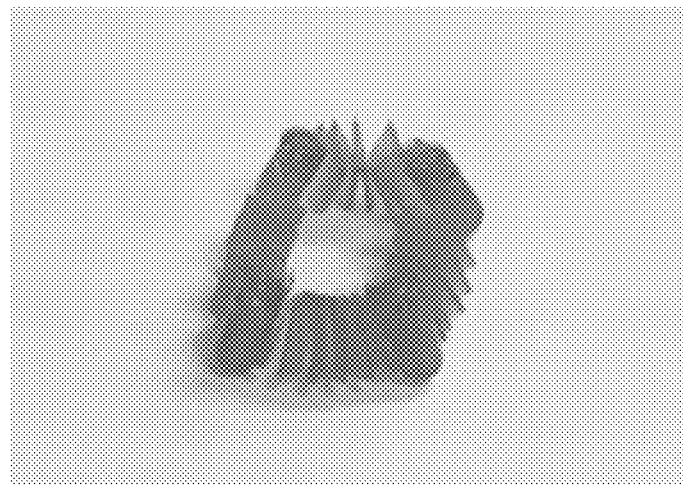
FIG. 3D is a perspective view of the expandable array of FIG. 3A in a substantially contracted state.

Another example of a cell culture array is shown in FIGS. 2A-2C in both expanded (FIG. 2B) and contracted (FIGS. 2A, 2C) states. The array 200 includes four receptacles 202, each receptacle including two beams 204. The beams 204 are shown in a corrugated configuration, extending between sides of the receptacles 202 to each neighboring receptacle. FIGS. 3A-3D illustrate contraction of the cell culture array 200 from an expanded configuration (FIG. 3A) through intermediary configurations (FIGS. 3B-C) to a shrunken configuration (FIG. 3D), each basket of the array having within it a liquid, which, as shown in the figures, does not spill as the array moves from the expanded state to the contracted state.

Mechanical transformation of the array can occur mostly on the connecting elements, or beams, rather than on the basket itself, so mechanical perturbation or disturbance to the culture inside each basket is minimal. In this process, the geometric expansion is achieved by stretching of the connecting members located between baskets (not the baskets themselves). In such a configuration, with little or no deformation in z-direction during a shape programming process (e.g., mechanical extension to the expanded state), there is likewise little to no contortion in the z plane during the shape recovery process (e.g., thermally-induced contraction to the contracted state).

The receptacles of an array can be formed of a same shape-memory polymer as that of the connecting members during the PµSL printing process. However, the baskets may alternatively be formed of a different material than that of the connecting members, including for example, a non-shape-memory material.

Furthermore, as illustrated, each basket is connected to each neighboring basket, with the internal baskets of the array of FIG. 1 each connected to each of its four neighboring baskets. In such a configuration, the mechanical force applied to each basket is symmetric, which can help to keep the basket in an upright orientation during expansion and contraction. However, the internal baskets of an array can be connected to fewer neighboring baskets, such alternating rows of missing beams in an x- or y-direction, or in the case of an irregularly shaped array, internal baskets may each have more than four neighboring baskets and, as such, more than four beams may be connected to each internal basked.

The transition temperature of the shape memory polymer can be tuned to a temperature that is (i) above the 37° C. cell culture temperature so that the basket array can retain its extended dimension during 3D cell culture and (ii) ≤50° C. or ≤80° C. as may be needed to prevent any thermal damage to the cell culture or tissue sample. Once the array returns to its originally printed/contracted configuration it can then be transferred to a paraffin-embedding histology cassette for subsequent fixation and paraffin-embedding processes. See (5)-(6) of FIG. 1.

Furthermore, a stiffness of the shape memory polymer can be tuned during the PμSL process such that it can be easily cut and sliced with a microtome after the paraffin embedding process.

The polymer can be an acrylate-based or methacrylate-based shape memory polymer. Such polymers advantageously provide for tunability in terms of elastic modulus, extent of deformation, and sensitivity to a stimulus that triggers glassy-rubbery transition. Chemical and thermomechanical characterization of the polymers can be assessed by Differential Scanning calorimetry (DSC), Fourier Transform Infrared (FTIR) spectroscopy, and/or Dynamic Mechanical Analysis (DMA) to ascertain an optimal combination of materials properties.

Figure 4A:
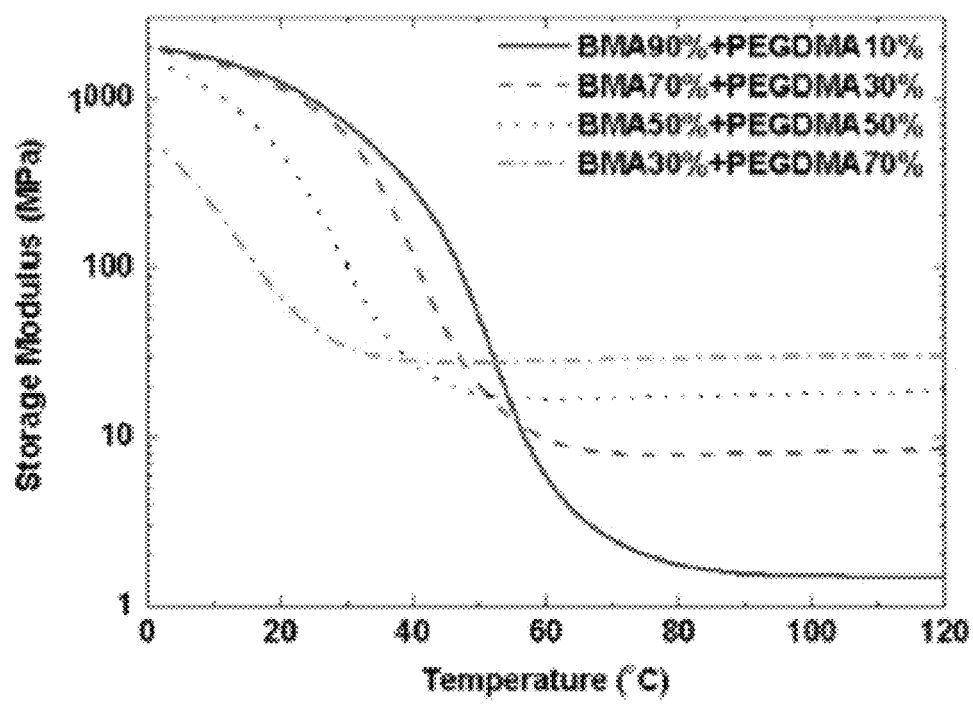
FIG. 4A is a graph of temperature dependent modulus change for four shape-memory polymers (SMPs), each of a different mixing ratio of benzyl methacrylate (BMA) and poly (ethylene glycol) dimethacrylate (PEGDMA).
Figure 4B:
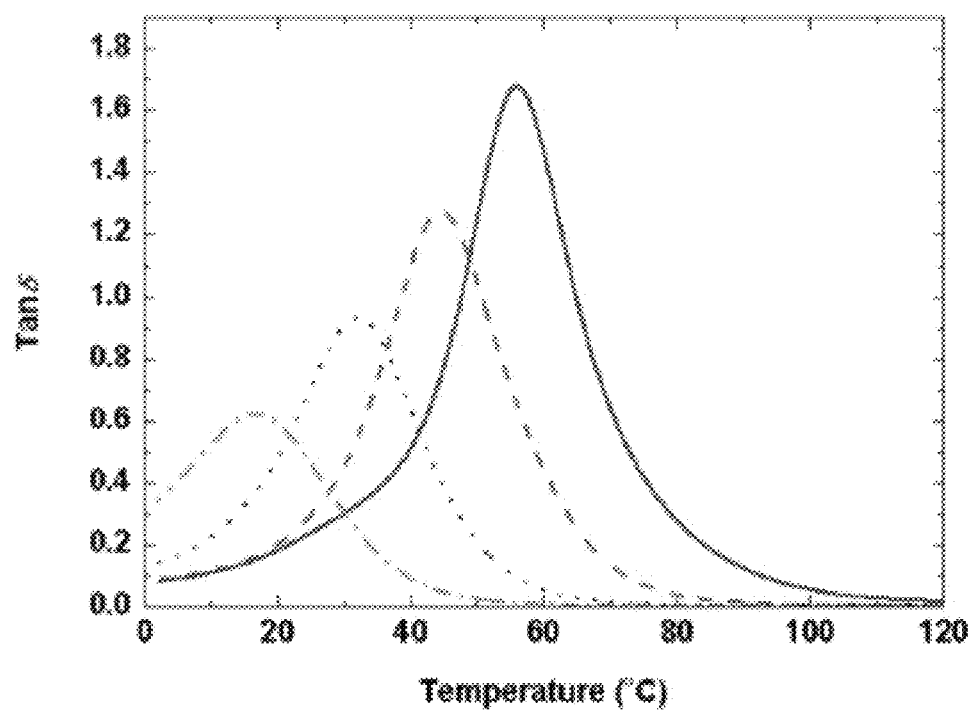
FIG. 4B is a graph of the shift of glass transition temperature ($T_g$) of the SMPs of FIG. 4A as measured by Dynamic Mechanical Analysis (DMA).
Figure 4C:
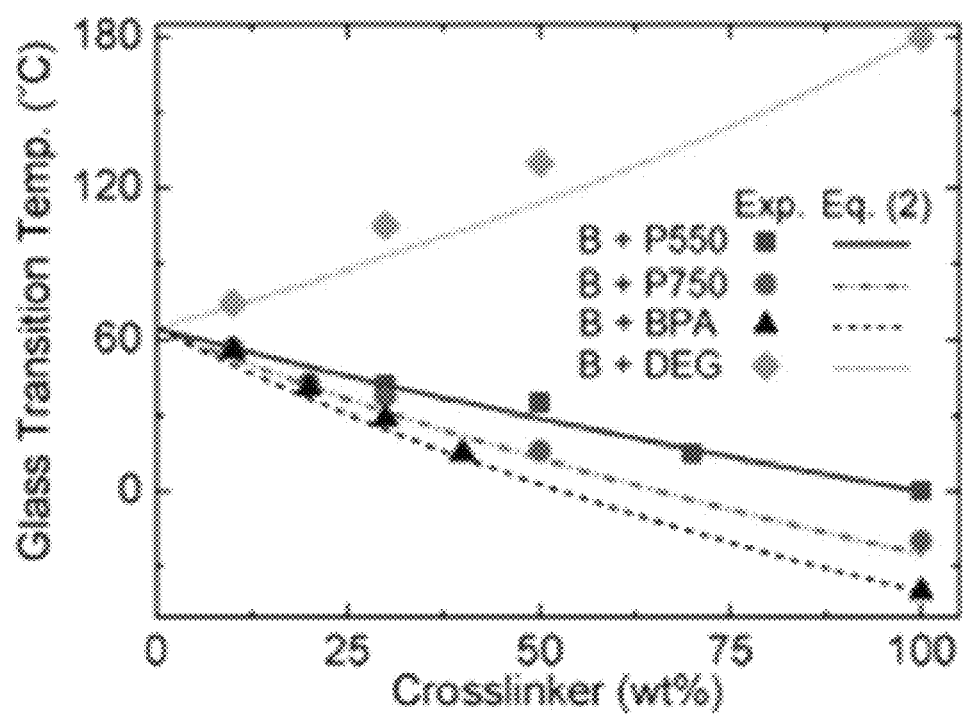
FIG. 4C is a graph of glass transition temperatures ($T_g$) of four SMPs as a function of percentage of crosslinker. In the legend, B stands for Benzyl methacrylate (BMA), P550 for Poly (ethylene glycol) dimethacrylate (PEGDMA) with molecular weight (Mw) 550, P750 for Poly (ethylene glycol) dimethacrylate (PEGDMA) with Mw 750, BPA for Bisphenol A ethoxylate dimethacrylate, and DEG for Di(ethylene glycol) dimethacrylate.

Preliminary results are shown in FIGS. 4A-4C for a shape-memory polymer (SMP) or varying composition. As shown in FIGS. 4A-4C, an elasticity of the SMP changes up to 3 orders of magnitude with a mild temperature change between 20° C. to 80° C. The effects of chemical composition, molecular weight of polymer, photo-initiator concentration and cross-linking density on the material's behaviors such as stiffness, strength, toughness, energy absorption, and glass transition temperature can be optimized to obtain desired material properties. The rubbery modulus $E_r$ of the polymer increases with an increase in crosslinking density as expected from entropic elasticity, $E_r=(3\rho RT)/M_c$; where, R is the gas constant, T is absolute temperature, $\rho$ is polymer density, and $M_c$ is average molecular weight between crosslinks. The ratio $\rho/M_c$ is the crosslinking density of the polymer network and can be obtained from a photo-polymerization model. Also, the Couchman equation [9] can be used to predict the glass transition temperature $T_g$ of the cured SMP from the prescribed ratio of SMP and cross-linker: $1/T=M_1/T_g^1+M_2/T_g^2$; where $T_g^1$ and $T_g^2$ are the glass transition temperatures of the respective pure-components, and $M_1$ and $M_2$ are the corresponding mass fractions of the SMP and crosslinker, respectively.

Experimental techniques including Fourier transform infrared spectroscopy (FTIR), Raman spectroscopy and Zetasizer can be used to characterize conversion ratio and molecular weight of the polymer. Experimental techniques including various microscopy, rheometer, differential scanning calorimetry (DSC), dynamic mechanical analysis (DMA), and thermo-mechanical analysis (TMA) can be used to characterize and assess the performance of synthesized materials. As such, a desired shape transformation at a desired temperature above or below cell culture temperature can be provided for an expandable array. Furthermore, a rubbery modulus can be tuned to a low value such that the receptacles, or baskets, or the array can be easily sectioned using microtomes. In addition, or alternatively, the SMP can be selected or configured to dissolve or degrade, for example, during histology processing.

Examples of suitable shape-memory polymers include polyacrylic acid, polyethylene glycol diacrylate, polyethylene glycol dimethacrylate, diethylene glycol dimethacrylate, bisphenol A ethoxylate dimethacrylate, tert-butyl acrylate, and n-Butyl methacrylate. The shape-memory polymer can be compatible with PμSL printing methods and can be tuned as described above.

As shown in FIGS. 1-3D, the beams connecting each of the receptacles of the array have a serpentine shape. However, other shapes are possible. For example, the shape can be pleated or corrugated, or otherwise include an undulating shape that permits both a lengthened and a contracted state. The number of folds, pleats, or turns of each beam, as well as the length of each beam can be adjusted to permit expansion and contraction to varying lengths. As such, expandable arrays can be customized to interface with multiwell plates or other cell-culturing/tissue collection vessels of varying shapes and sizes. Placement of the beams with respect to the receptacles can also be customized to accommodate various cell-culturing and tissue collection vessels. For example, for a multiwell plate, beams may be disposed to extend from an upper surface of the receptacles to enable the receptacles to be disposed within the wells without or with minimal beam interference. In another example, beams may be disposed to extend from a lower surface of the receptacles to accommodate a hanging cell culture apparatus.

Figure 5A:
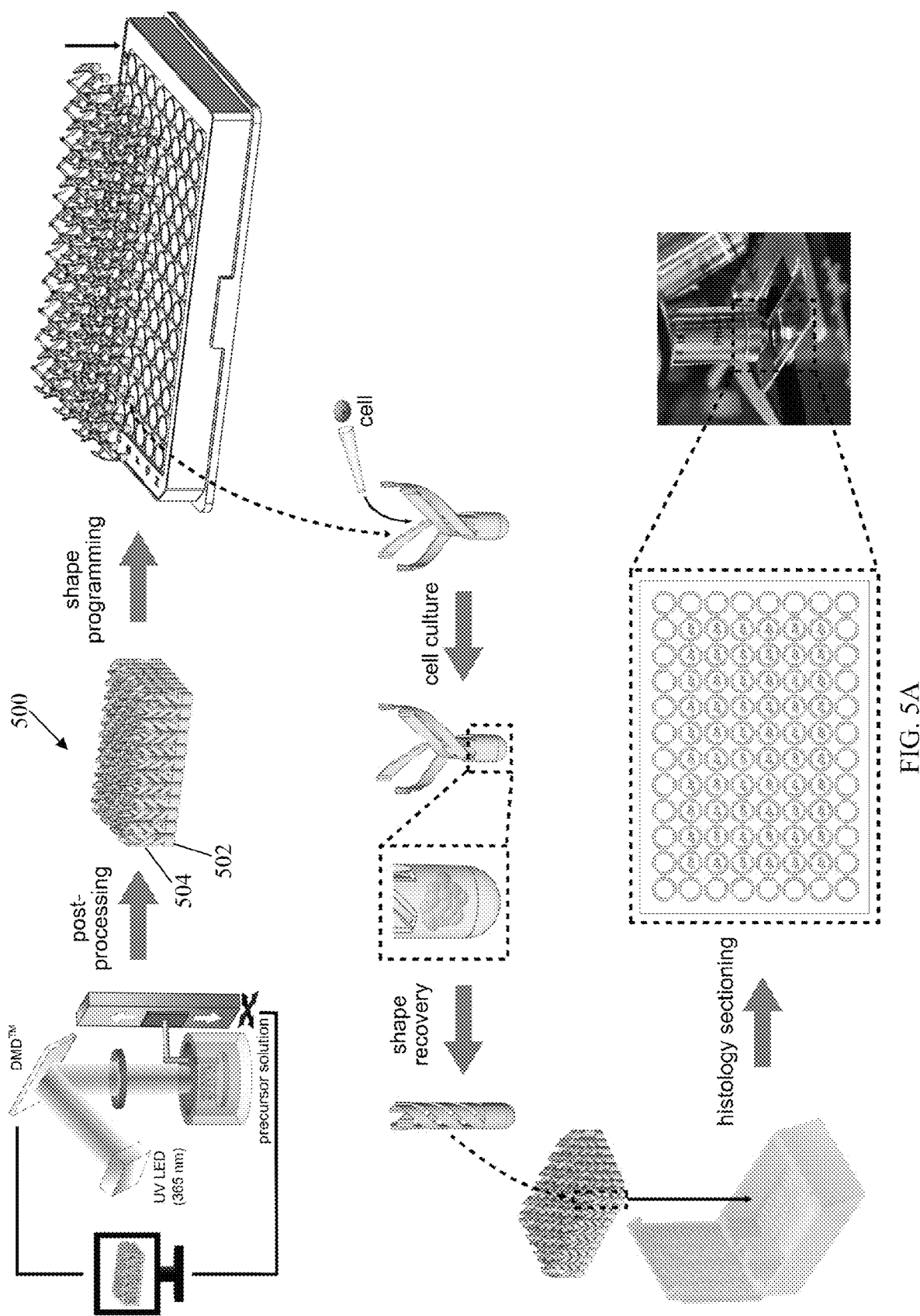
FIG. 5A is a schematic of another example of an expandable array and example methods of making and using same.
Figure 5B:
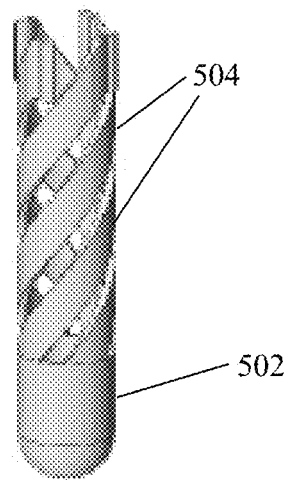
FIG. 5B illustrates an example of a receptacle that includes connecting beams in a contracted state.
Figure 5C:
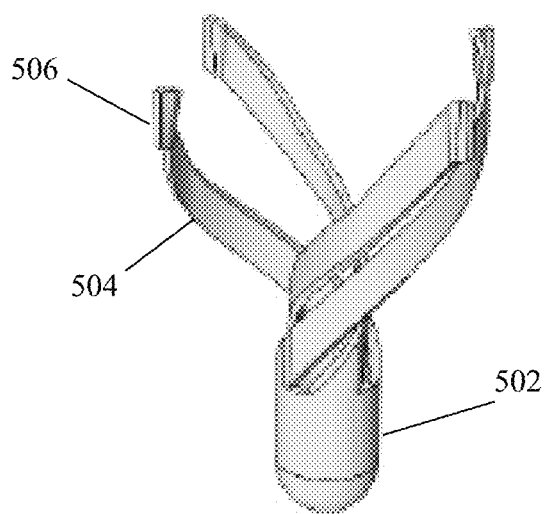
FIG. 5C illustrates the receptacle of FIG. 5B with connecting beams in an expanded. or extended, state.

Another example of an expandable array is shown in FIGS. 5A-5C. The array 500 includes a plurality of receptacles 502, or cell tubes, having beams 504 in a helical bridge configuration. The helical bridges 504 are shown in a contracted state in FIG. 5B and in an expanded state in FIG. 5C. The helical bridges 504 can include a joining element 506 disposed at an end of each beam for connection to a neighboring beam, for marker placement, or both. Upon stretching of the array 500, the helical bridges 504 can unwind to accommodate a dimensional change, as illustrated in FIG. 5A. When heated, the helical bridges 504 can revert to their original shape.

The receptacle and beam configuration shown in FIGS. 5A-5C can advantageously provide for larger-volume receptacles over the configuration shown in FIG. 1 as the beams are disposed above, rather than between, the receptacles in the contracted state.

For conventional, multiwell plates, such as a 96-well, 24-well, or 6-well plate, the expandable array can include a plurality of receptacles that are arranged in, respectively, an 8×12, 4×6, or 2×3 array. For a conventional histology cassette, the expandable array can have a width of about 20 mm to about 30 mm (e.g., 24 mm) and a length of about 25 mm to about 35 mm (e.g., 30 mm) when each beam is in the contracted state.

The receptacles of an expanded array can also vary to interface with the size and shape of the intended cell-culturing/tissue collection vessel. For a conventional multiwell plate, for example, it may be desirable to have each receptacle comprise a basket-like shape, with a bottom of each basket located approximately 2 mm above a bottom of the plate well. For such a conventional multiwell plate, each receptacle of an expandable array can have a diameter of about 0.5 mm to about 1.5 mm (e.g., 1 mm), a depth of about 5 mm to about 15 mm (e.g., 11 mm), and a wall thickness of about 50 μm to about 150 μm (e.g. 100 μm).

Expandable arrays can be included within a kit that further includes materials for cell-culturing, such as one or more biomolecules (e.g., a growth factor, an extracellular matrix component) and/or a cell culture medium or ingredients for making a cell culture medium.

Figure 8:
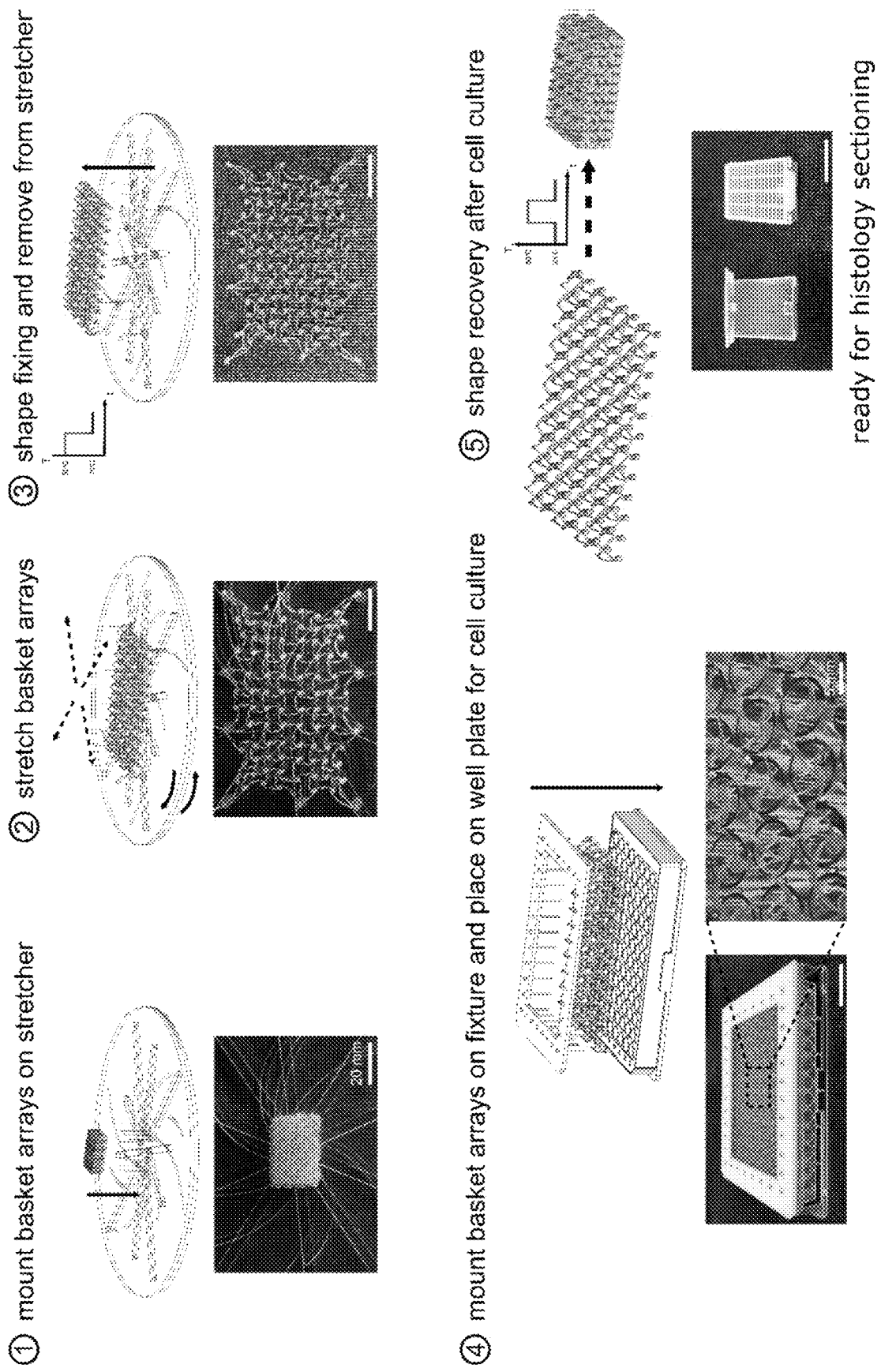
FIG. 8 illustrates a process for operation of an expandable array.
Figure 9A:
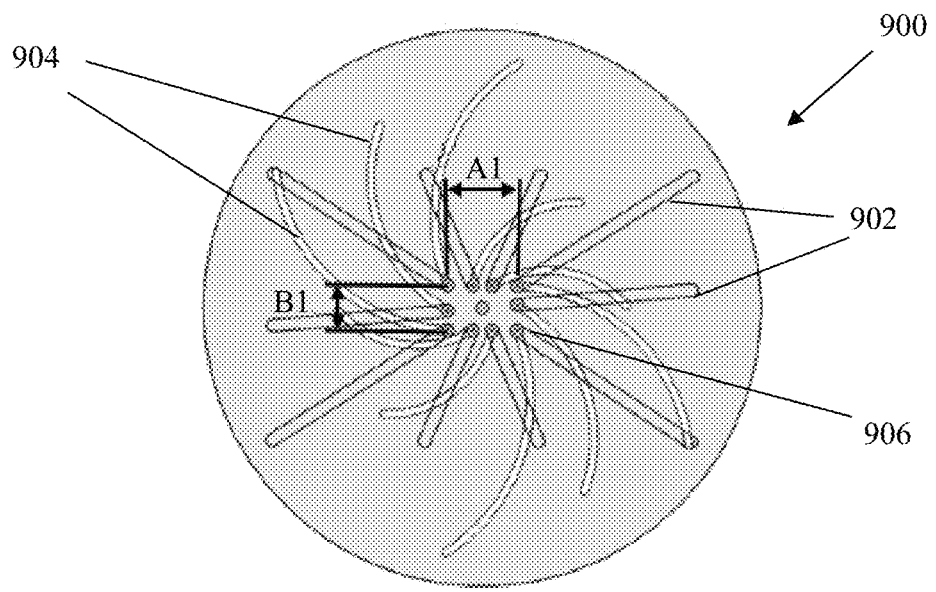
FIG. 9A is a schematic illustrating an expandable array mounted within a stretcher in an initial, contracted configuration.
Figure 9B:
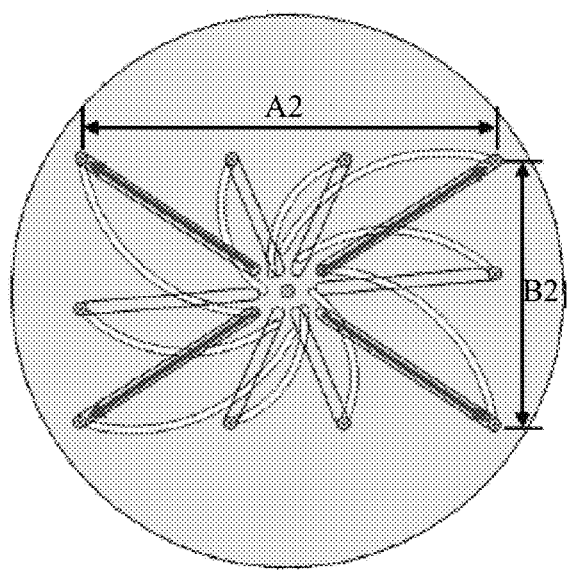
FIG. 9B is a schematic illustrating the expandable array and stretcher of FIG. 9B in an expanded configuration.
Figure 9C:
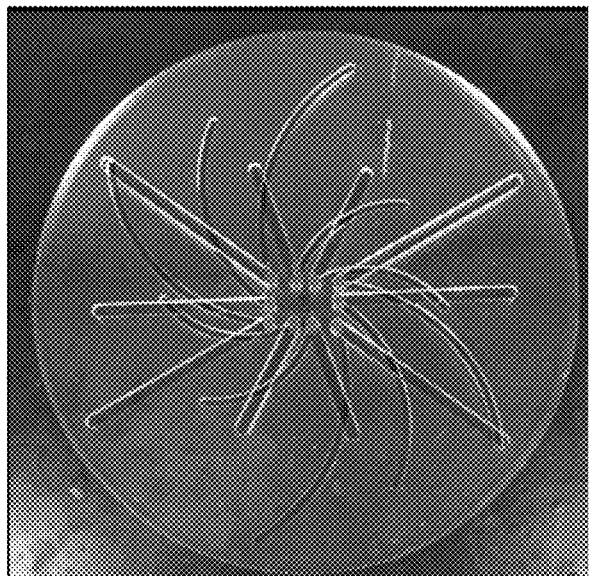
FIG. 9C depicts an example array mounted within an example stretcher in the configuration shown in FIG. 9A.

Stretching of expandable arrays can optionally be performed by a stretching device, alternatively referred to as a stretcher. An example of a stretching device is shown in FIGS. 9A and 9B, and use of the device is shown in FIG. 8. A top plate of the stretcher 900 includes a plurality of straight rails 902; and, a bottom plate of the stretcher 900 includes a plurality of curved rails 904 (shown in transparency in FIG. 9A). As illustrated, the patterns of rails connect locations of distributed baskets 906 of dimensions A1 and B1 in a compact state and A2 and B2 in an expanded state. The rails of the upper plate of the stretcher 900 can be of a width to accommodate a diameter of a top portion of an expandable array, and rails of the lower plate can be of a width to accommodate a diameter of a bottom portion of an expandable array. Outer baskets of the array sitting in both rails can move from a compact configuration to an expanded configuration by rotating the top plate against the bottom plate, as shown in FIG. 9B.

Figure 10A:
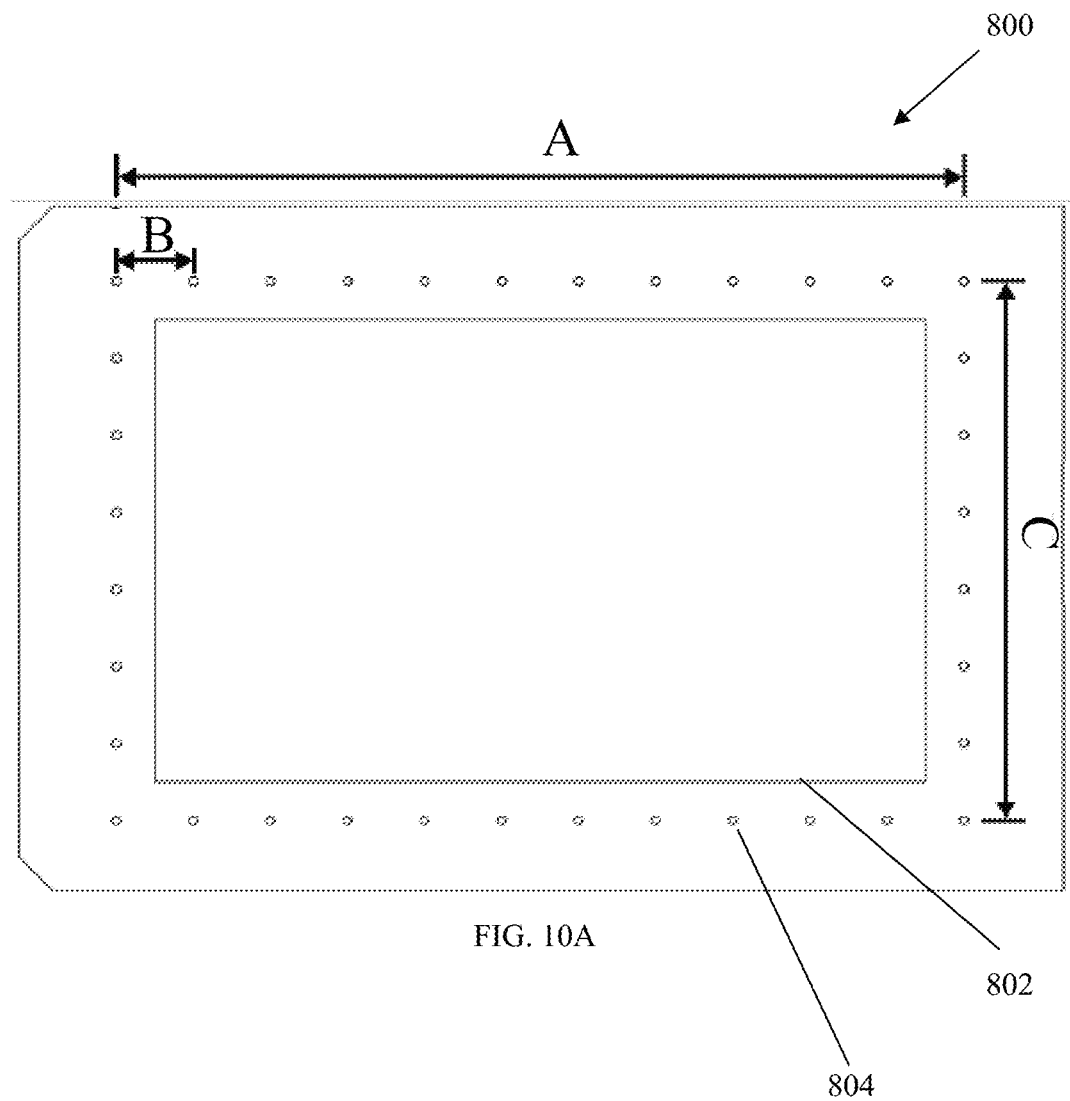
FIG. 10A is a schematic illustrating a top-side view of a plate fixture.
Figure 10B:
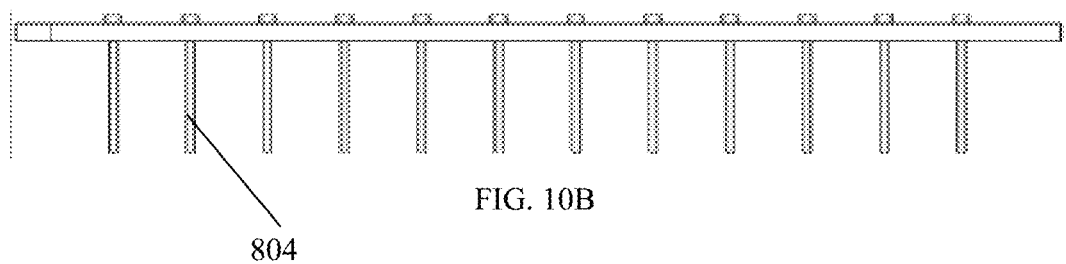
FIG. 10B is a schematic illustrating a side view of the plate fixture of FIG. 10A.

Expandable arrays can optionally be placed in a fixture device prior to placement within a histology cassette, or other vessel. An example of a fixture 800 is shown in FIGS. 10A and 10B. The fixture can have dimensions A×C corresponding to widths of a histology cassette, or other containing vessel in which an expandable array is to be placed. A window 802 can be included in the fixture for viewing of the array. The fixture can further include pins 804 configured to align baskets disposed around an edge of an array with edge wells of a multi-well plate. For example, a distance B between pins can be about 9 mm, corresponding to a distance between wells of a 96-well plate. Fixtures can advantageously prohibit or restrain the SMD of the expandable array from contracting to its compact state during cell culturing processes.

Methods of making expandable cell culture arrays can include PμSL techniques, as shown in FIGS. 1 and 5A. In particular, the method can include discretizing a 3D computer-aided design (CAD) model of the receptacles and beams of an array and displaying the discretized images on a digital micromirror (DMD™) device to apply a dynamic virtual photomask. UV light, such as illimitation from a light emitting diode (LED), is reflected off the dynamic mask and focused on a surface of a photocurable liquid polymer through a projection lens to form a layer of the array. The arrays can then be built, layer upon layer, by repeating the process under all layers are completed. While PμSL techniques are described in the following Example, other additive manufacturing techniques or molding techniques can be employed for manufacture of cell culture arrays.

Methods of operating expandable cell culture arrays can include uniformly stretching the arrays to the dimensions of a well plate. The cell culture arrays can thereby be programmed to retain the dimensions of the well plate. The programmed cell culture arrays can then be transferred to the well plate with a one-to-one matching of the receptacles of the array and the wells of the plate. Cells, cell culture media, drug compositions, and other materials, or any combination thereof, can then be placed within the receptacles. For cell culturing, upon cell seeding within the receptacles of the array, the well plate, including the array, can be placed in an incubator or oven for cell culturing. To fix cells within the receptacles, formalin can be introduced. The array can then be removed from the well plate and heated to a shape recovery temperature to cause the array to revert to a compact (e.g., printed) configuration. For histology processing the compact configuration of the array can be of a dimension that fits within a histology cassette. The array, including cell contents can then be transferred to the histology cassette. Paraffin wax or other material can then be introduced prior to sectioning. Sectioning can be performed, such as with a microtome to obtain thin, cross-sectional films for analysis.

While example arrays have been described as receiving biological samples, expandable arrays may also be configured to receive non-biological samples, and methods of using such expandable arrays can include placing a non-biological sample within the receptacles of the array.

Furthermore, while 3DP techniques have been described as methods by which expandable arrays may be manufactured, molding processes may instead be applied to create such expandable arrays.

Expandable arrays can include other programmable materials that enable connecting beams of the array to transition from an expanded state to a contracted state. For example, the programmable material can be a magnetoactive material. Magnetoactive materials are materials that can be programmed to respond to magnetic fields, such as with a large deformation or tunable mechanical properties. Examples of magnetoactive materials include elastomers or other polymers within which magnetic or magnetizable particles are disposed. With connecting beams comprising a magnetoactive material, the application or adjustment of a magnetic field can provide a stimulus that initiates contraction of the array.

Figure 17:
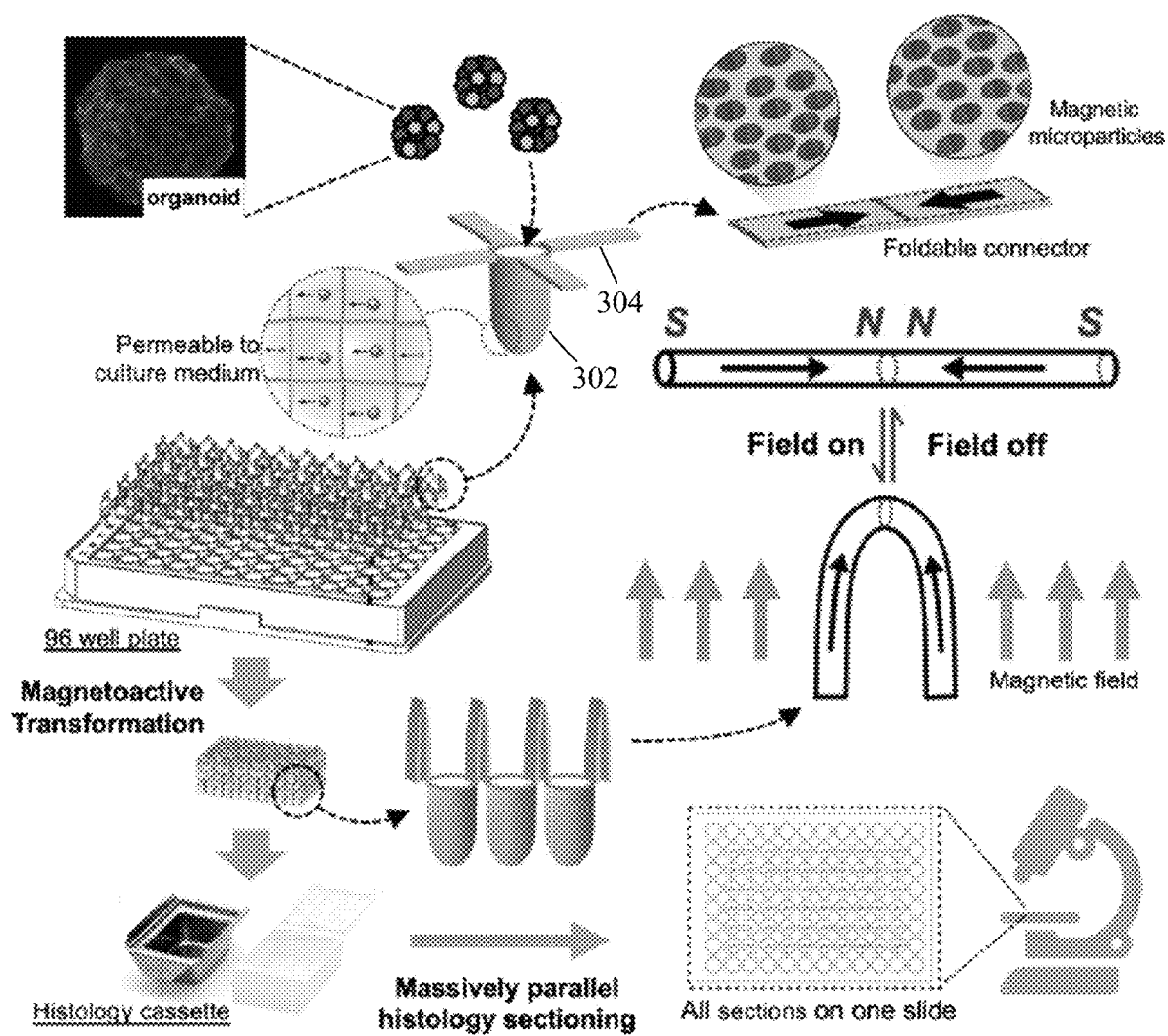
FIG. 17 is a schematic of another example of an expandable array and methods of using same.
Figure 18A:
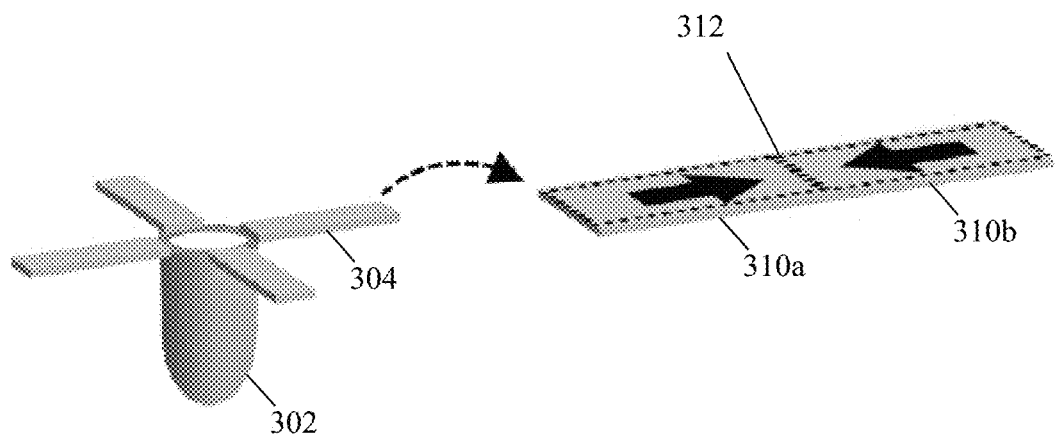
FIG. 18A illustrates an example of a receptacle that includes connecting beams in an expanded state.
Figure 18B:
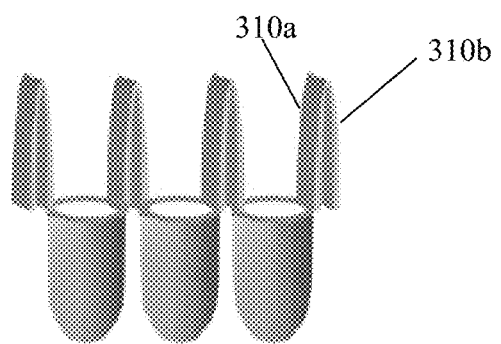
FIG. 18B illustrates an example of receptacles as in FIG. 18A with connecting beams in a contracted state.

As shown in FIGS. 17 and 18A-18B, an array (such as arrays 100, 500) can include a plurality of receptacles 302 connected to one another by beams 304 that comprise a magnetoactive material. The beams 304 can include at least two sections 310a, 310b programmed to have an opposite magnetic orientation. FIG. 18A illustrates the connecting beams in an extended state, and FIG. 18B illustrates the connecting beams in a contracted state. In an extended state, the beams 304 extend substantially horizontally between neighboring receptacles 302. Upon application of a magnetic field, the connecting beams responsively fold into the contracted state. The fold can occur at a location 312 at which the magnetic orientation of the material transitions from that of section 310a to that of section 310b.

While the example receptacles and beams of FIGS. 17 and 18A-18B are illustrated to provide for a single fold, additional folds can be included. For example, the connecting beams can include more than two sections of differing magnetic orientations. Three, four, five, six or more sections can be programmed to have differing or alternating magnetic field orientations, thereby allowing the connecting beam to adjust to a corrugated shape upon contraction. As illustrated, the connecting beam is programmed to fold vertically; however, the beams can be configured to respond by adjusting to other configurations. For example, the beams can comprise the geometric structures shown in FIGS. 1 and 5, with application of a magnetic field causing the beams to fold horizontally or to migrate upwards to a more compact helical configuration.

As illustrated, a magnetic field can be applied by, for example, a magnet placed above or proximate to the array. The programmed orientation of magnetic (e.g., ferromagnetic) microparticles embedded within the elastomer or polymer material can provide for transitions between substantially unfolded (e.g., flat) and substantially folded states, depending upon orientation of the applied magnet. The transition between these states can be reversible. As illustrated, an applied magnet can be flipped with respect to the array such that it is either attracting or repelling the magnetic microparticles, the magnetoactive material responsively causing folding or unfolding of the connecting beams. Once in the folded, or otherwise contracted, state, the array can be transferred, for example, to a histology cassette, as described above.

Structural features of arrays comprising magnetoactive materials can be similar to those described herein with respect to shape-memory polymers. In particular, the arrays can be of any configuration (e.g., an 8×12, 4×6, or 2×3 configuration, a configuration with handle(s) disposed at a perimeter of the array, etc.) with beams and receptacles of various shapes, sizes, and dimensions (e.g., rounded-bottom receptacles, mesh receptacles, etc.).

Methods of using arrays comprising magnetoactive materials and methods of maintaining biological samples with such arrays are also similar to those described herein with respect to shape-memory polymers, differing in that the application of a stimulus includes exposure of the array to a magnetic field in place of light or heat.

An expandable array can provide for a direct transfer of a large cell-culture array from a standard multi-well plate to a histology cassette as a single specimen. The direct transfer can be particularly helpful for organoid cultures. Organoids are multi-cellular 3D cell cultures of stem cell-derived, self-organizing miniature organs that replicate the key structural and functional characteristics of their in vivo biology. Due to their ability to emulate microarchitecture and functional characteristics of native organs, organoids are emerging as a promising approach for the modeling of development of various human organs and pathologies. Microscopy is a powerful tool for the analysis of organoids because it reveals the spatial arrangement and biological heterogeneity within the organoid. However, it must be preceded by histology sectioning that requires slow, laborious, and mostly manual process of harvesting organoids, converting them into histology specimens, embedding them in paraffin wax, slowly sectioning through the specimen using a microtome to locate the multi-cellular aggregates, and then staining to give contrast to the tissue as well as highlighting particular features of interest. In particular, when a microwell plate is employed for culturing and assaying a large number of organoids for drug screening, a series of repetitive histology sectioning for individual organoids canimpede effective analysis. In addition to increasing labor costs for histology specialists, the slow and serial nature of the processing steps is also a major roadblock to rapid and effective drug discovery for aggressive tumors such as glioblastoma.

Expandable arrays can significantly improve the time and effort involved in processing organoid samples for histology. As shown in FIGS. 1 and 17, at the end of a cell culture process. The expandable array containing three-dimensional (3D) organoid cultures can be removed from a multi-well plate as a single unit and collapsed to a footprint approximately four-times smaller (e.g., from dimensions of about 110 m×65 mm for a 96 well plate to about 30 m×20 mm for a histology cassette). As a result, the entire array of cultured organoids can be directly transferred to a histology cassette as a single specimen while preserving the registry and orientation of the organoids. Subsequent paraffin embedding and histology sectioning can yield an ordered array of organoid sections deposited onto a single microscope slide. The processing of all 96 sections in parallel eliminates the need for 96 repetitions of the routine histological analysis processing steps, which can take several days to weeks for an array of such size.

Expandable arrays comprising magnetoactive material can provide for transition of the array through exposure to a magnetic field, which can be provided by a handheld magnet and which does not require particular lighting and heating equipment to transition the array to its contracted state. The application of a magnetic field can further provide for minimal, if any, influence on the biological samples contained within the array receptacles. Magnetic stimulation can provide for a fast, non-contact, and non-cytotoxic stimulus for transition the array to its contracted state. Furthermore, the receptacles of an expandable array can be formed from a different material than the magnetoactive material comprising the connecting beams, thereby providing for minimal disturbance to the biological samples during transition of the array to its contracted state as the receptacles remain structurally unaffected by application of the magnetic field.

Figure 19:
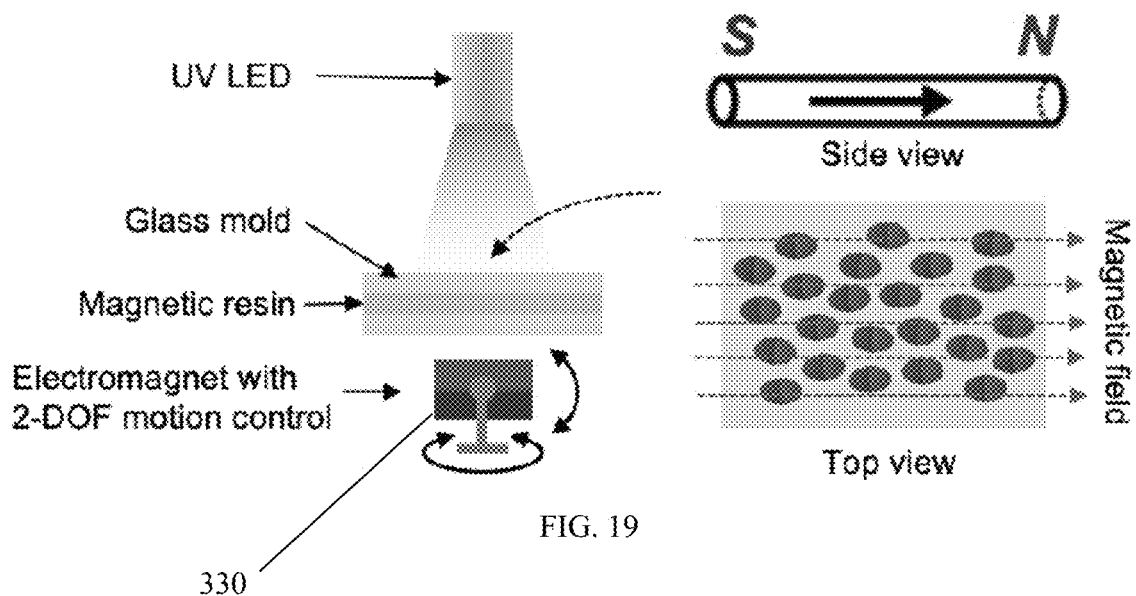
FIG. 19 is a schematic illustrating a method of programming a magnetic orientation of magnetoactive material for connecting beams of an array.

The expandable arrays can be created by multi-material digital 3D printing techniques (e.g., projection microstereolithography (PµSL)). In particular a 3D printable magnetoactive smart material can be synthesized, as shown in FIG. 19. A composite resin can be prepared using a photo-curable polymer (e.g., poly(ethylene glycol) diacrylate, PEGDA), a photo-initiator (e.g., Irgacure 819), and ferromagnetic microparticles (e.g., neodymium-iron-boron, NdFeB). The resin composition can be adjusted to provide for a desired viscosity, dispersion, reactivity, and magnetic sensitivity. Magnetic sensitivity can be measured or confirmed by a rheometer, Fourier-transform infrared spectroscopy (FTIR), and dynamic mechanical analysis. A UV curing testbed with a variable magnetic field generator 330 can be used to provide selective magnetization of a resin. As illustrated, the magnetic field generator can include an electromagnet with at least two degrees of freedom (DOF) for motion control. By changing field direction and curing the selected region with UV, different areas can be programmed to have different magnetization orientation, resulting in a prescribed transformation with a magnetic field (e.g., folding transformation as shown in FIG. 17).

Figure 20:
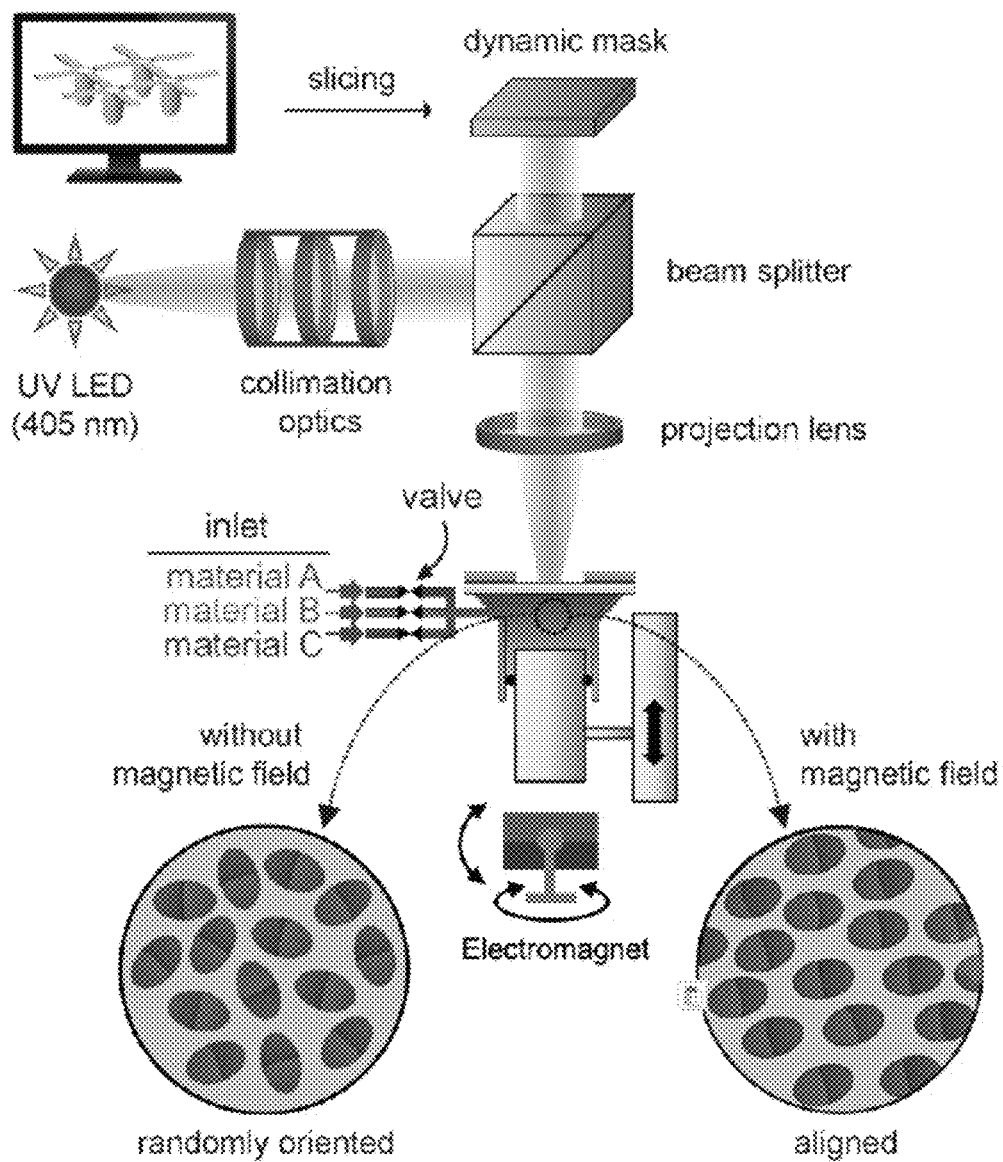
FIG. 20 is a schematic illustrating a method of magnetic-field-assisted multi-material 3D printing for in-situ magnetic programming of magnetoactive material.

As illustrated in FIG. 20, a PµSL system can be modified to include a variable magnetic field generator. Strength and direction of a magnetic field can be controlled around the printing chamber, where material can be readily changed as needed. Such a system can provide for flexibility in printing an array comprising multiple materials. For example, receptacles of the array can be printed with a first material providing for biocompatibility while connecting beams of the array are printed with a second, magnetically-programmable material. Inclusion of an electromagnet can provide for in-situ magnetic programming of the smart material. Performance and functionality of a smart cell-culture array comprising a magnetoactive material can be evaluated by real-time by monitoring of the magnetic field and associated deformation. A 3D printed array can be soaked in acetone followed by an ethanol wash and sterilization to remove residual photo-chemicals.

While a PµSL system is shown and described, manufacture of arrays comprising magnetoactive materials is not limited to such systems. As material selection can be expanded over arrays comprising shape-memory polymers, other manufacturing methods can be employed. For example, the arrays can be formed by injection molding, providing for improved scalability and higher throughput over PµSL techniques.

The receptacles can be formed with, for example, PEGDA, which is biocompatible, permeable to culture medium, non-adherent to cells, and 3D printable or moldable. Other suitable materials for receptacles include 1,6-Hexanediol diacrylate (HDDA), Polyacrylamide (PAAm), and Poly(2-hydroxyethyl methacrylate) (pHEMA).

The connecting beams can be printed with a magnetoactive material as described above. While the connecting beams may comprise a same biocompatible polymer as provided for the receptacles, other polymer or elastomer materials, including non-biocompatible materials, can be used instead. The polymer or elastomer material can be any material within which magnetic or magnetizable structures can be embedded. Examples of suitable polymer or elastomer materials include Polydimethylsiloxane (PDMS) and Polyurethane (PU).

The magnetic or magnetizable structures can be ferromagnetic or ferrimagnetic and can be in the form of particles, such as microparticles. Examples of suitable magnetic materials include neodymium-iron-boron (NdFeB), samarium cobalt (SmCo), alnico (AlNiCo), ferrite ($Fe_3O_4$), and Chromium (IV) oxide (CrO2). In another example, the magnetoactive material can comprise a magnetic rubber, such as a synthetic rubber or polyvinyl chloride (PVC) impregnated with a ferrite powder (e.g., barium, strontium).

A concentration and size of magnetic particles embedded within the polymer can vary to provide for an appropriate level of material flexibility and level or response to a magnetic field stimulus. In general, magnetic particles of smaller sizes can provide for denser magnetic lattices within the polymer material and, consequently, greater magnetic response. The magnetic particles can be microparticles or nanoparticles. For example, the magnetic particles can have diameters of about 0.5 µm, 1 µm, 5 µm, 10 µm, 25 µm, or 50 µm. A concentration of magnetic particles within the polymer material can be about 1%, 5%, 10%, 15%, 20%, or 30% by volume. The particles can be monodispersed throughout the polymer comprising the connecting beam.

Example 1

4D Cell-Culture Arrays

Expandable arrays were created for cell culturing, the expandable arrays configured to transform between the size of a histology cassette and the size of a 96-well plate (e.g., 3.6× the size of the histology cassette) while maintaining a same layout in both forms. Expandable arrays were manufactured and operated according to the procedure shown in FIG. 5A.

Projection Micro-Stereolithography (PµSL)

PµSL techniques were employed for the manufacture of the cell-culture arrays. The resolution of the digital dynamic mask was 1920×1080 and the projection area was 24×14 mm, providing for a nominal resolution of 13 µm. A resolution of 800×800 (~10 m×10 mm) was used in printing to ensure high uniformity in light intensity. To print full basket arrays with a dimension of 30 m×20 m×11.2 mm, a 3-by-2 stitching of projections within one layer was employed (horizontal movement of printed structure using XY stages).

A custom-built PµSL system was used in this work. It consisted of a UV LED (365 nm) (L10561,Hamamatsu), a collimating lens (LBF254-150, Thorlabs), a digital micromirror device (DMDTM) (DLPLCR6500EVM, Texas Instruments), three motorized linear stages (MTS50-Z8, Thorlabs), and a projection lens (Thorlabs). Printing parameters we used include a light intensity of 29 mW cm-2, a layer thickness of 50 and a curing time of 1 s. The entire PµSL system was kept in a UV blocking enclosure.

Shape Memory Polymer (SMP) Materials

Shape memory polymer (SMP) was included as a constituent material of the 3D cell-culture basket arrays to enable transformation between configurations.

All chemicals, including liquid oligomers, photoinitiator (PI), and photo absorber (PA), were purchased from Sigma-Aldrich (St. Louis, Mo., USA) and used as received. Poly (ethyleneglycol) diacrylate (PEGDA) (Mn250) and Bisphenol A ethoxylate dimethacrylate (BPA) (Mn1700) were mixed at a ratio of 9:1 in weight. Phenylbis(2,4,6-trimethylbenzoyl) phosphine and Sudan I were added at the concentration of 2 wt. % and 0.1 wt. % of the precursor solution as PI and PA, respectively.

Post Processing

After printing, the arrays were treated using post-processing procedures prior to cell culturing processes.

Printed structures were rinsed in fresh ethanol for 30 s for 3 times to remove any uncured precursor solution. After being dried in air until the absorbed ethanol evaporated, the structures were rinsed in pentane one more times to avoid adhesion between bridges and baskets. After pentane drying, the structure were post-cured in a UV oven (CL-1000L, UVP, 365 nm) for 2 hours to polymerize all unreacted ethyl group in acrylate/methacrylate . To eliminate toxicity in remained PI and PA, fully crosslinked structures were stored in an Acetone bath for 5 days. Structures taken out from the Acetone bath were rinsed in ethanol one more time for sanitization and were dried overnight at room temperature.

Dynamic Mechanical Analysis and Failure Strain

To characterize the SMP's thermomechanical properties, a photocurable precursor solution was prepared using Poly (ethylene glycol) diacrylate (PEGDA) and bisphenol A ethoxylate dimethacrylate (Mn-1700) (BPA). Upon photopolymerization, a cross-linked polymer network is formed with these two materials. It has been shown that a glass transition temperature $T_g$ can be tailored by using different ratios of monomer and crosslinker. To maintain shape fixity at 25° C. (e.g., room temperature) and trigger shape recovery at 50° C. (e.g., an accepted maximum temperature for cell viability), the SMP was designed to have a weight ratio between PEGDA and BPA of 9:1. Thermomechanical properties of the SMP were then characterized by dynamic mechanical analysis (DMA) tests on both 3D printed and molded specimens.

For molded samples, an SMP precursor solution without PA was injected into a mold of two glass slides separated by 1 mm spacers. Glass slides were cleaned with ethanol and coated with RainX for easy demolding. The precursor solution in the mold was cured in a UV oven (CL-1000L, UVP, 365 nm) with a light intensity of 5 mW cm-2 for 20 min, yielding a fully crosslinked polymer film with a thickness of 1 mm. Samples were laser cut to 40 m×8 mm×lmm rectangular specimens. For 3D printed samples, the same printing parameters and post-processing procedure (except toxicity-eliminating steps) were used. Dimensions of 3D printed samples were 25 m×8 m×1 mm. DMA was conducted on a dynamic mechanical analyzer (Q800, TA Instruments) using a tensile loading mode. Testing parameters for DMA included strain of 0.2%, frequency of 1 Hz, preload of 0.001 N, and force track of 150%. Specimens were heated at 25° C. for 10 min prior to each test. Storage modulus, loss modulus, and tan δ were measured as a function of temperature while temperature was increased to 75° C. at a rate of 1° C. min$^{-1}$.

Figure 6A:
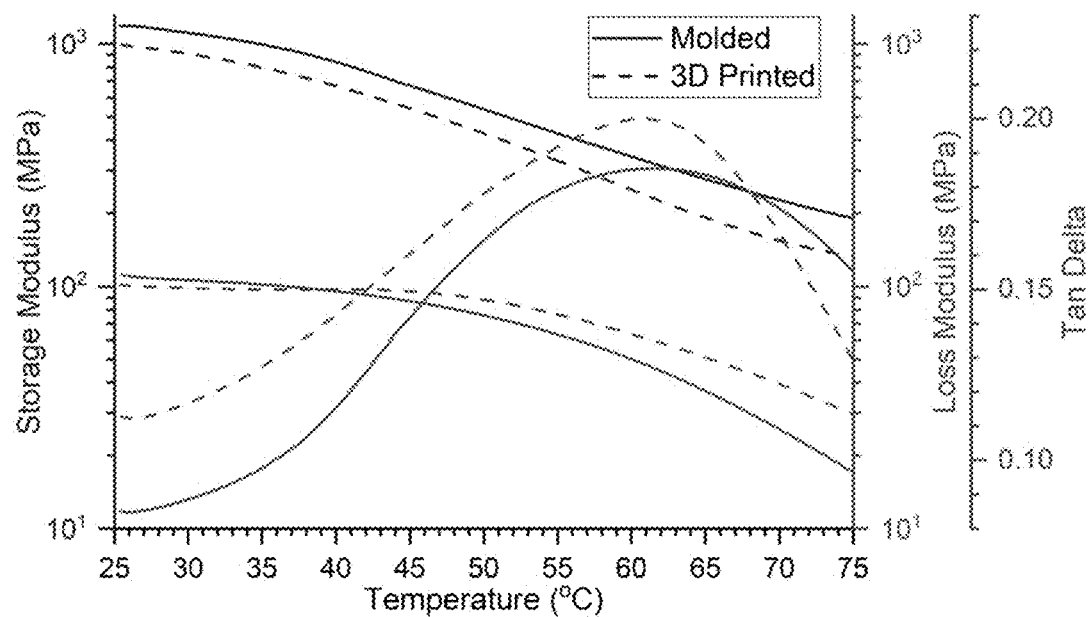
FIG. 6A is a graph of storage modulus and loss modulus versus temperature from a dynamic mechanical analysis (DMA) of 3D-printed and molded specimens of a shape memory polymer (SMP).

The results from DMA tests on both specimens are shown in FIG. 6A. Note that the storage modulus of the SMP changes from 984 MPa at 25° C. to 132 MPa at 75° C. Tan δ indicates that the SMP has a $T_g$ of 61° C. Though $T_g$ is higher than a maximum heating temperature of 50° C., recovery behavior was observed at 50° C. and high $T_g$ is desired to for better shape fixity at room temperature.

For temperature dependent failure strain tests, molded films were made using the same protocol from the DMA test. The molded films were laser cut into a dog-bone shape (gauge section: 16.5×3×1 mm) to measure strain at failure of material at different temperatures. Two grippers clamped on two ends of rectangular specimens. An air chamber with Peltier heater (CP-061HT, Technology, Inc.) underneath was used to control temperature inside and a thermocouple connected to an NI temperature module on cDAQ (NI 9171 and NI 9211, National Instrument) was used to measure temperature. Two dots were marked in the gauge section of dog-bone specimens and a digital camera (Canon 60D) were set on top to monitor distance between dots. One gripper was then manually moved at an average speed of 0.2% $sec^{-1}$ to stretch the sample until failure. Strain at failure was then calculated using final distance divided by initial distance between two dots.

Figure 6B:
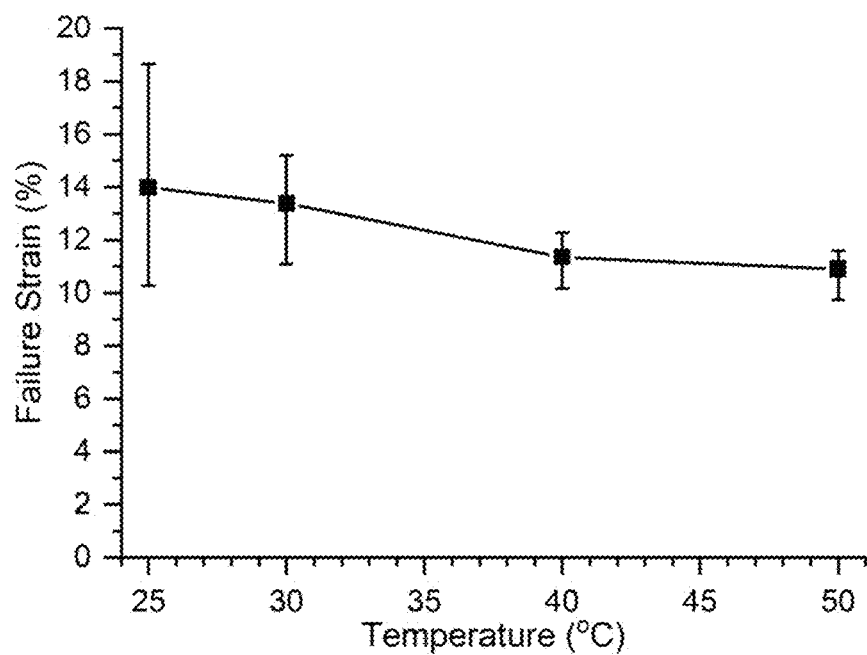
FIG. 6B is a graph of failure strain versus temperature from a tensile test of laser-cut molded specimens of the SMP.

Using the molded specimens that were laser cut into dog-bone shape, stretchability of the SMP was tested by tensile test at four different temperatures, the results of which are shown in FIG. 6B. During basket arrays' transformation from histology cassette configuration to 96-well plate configuration, a global dimensional change of 3.6 times was required. Adequate stretchability can be an important design constraint for limiting local strain to avoid breakage during transformation. Four different temperatures between 25° C. to 50° C. were tested. Average stretchability at each tested temperature varied from 12% to 14%, and minimum stretchability among all measurements was slightly above 10%. The result indicates local deformation during shape transformation should be limited within 10% of strain.

Figure 6C:
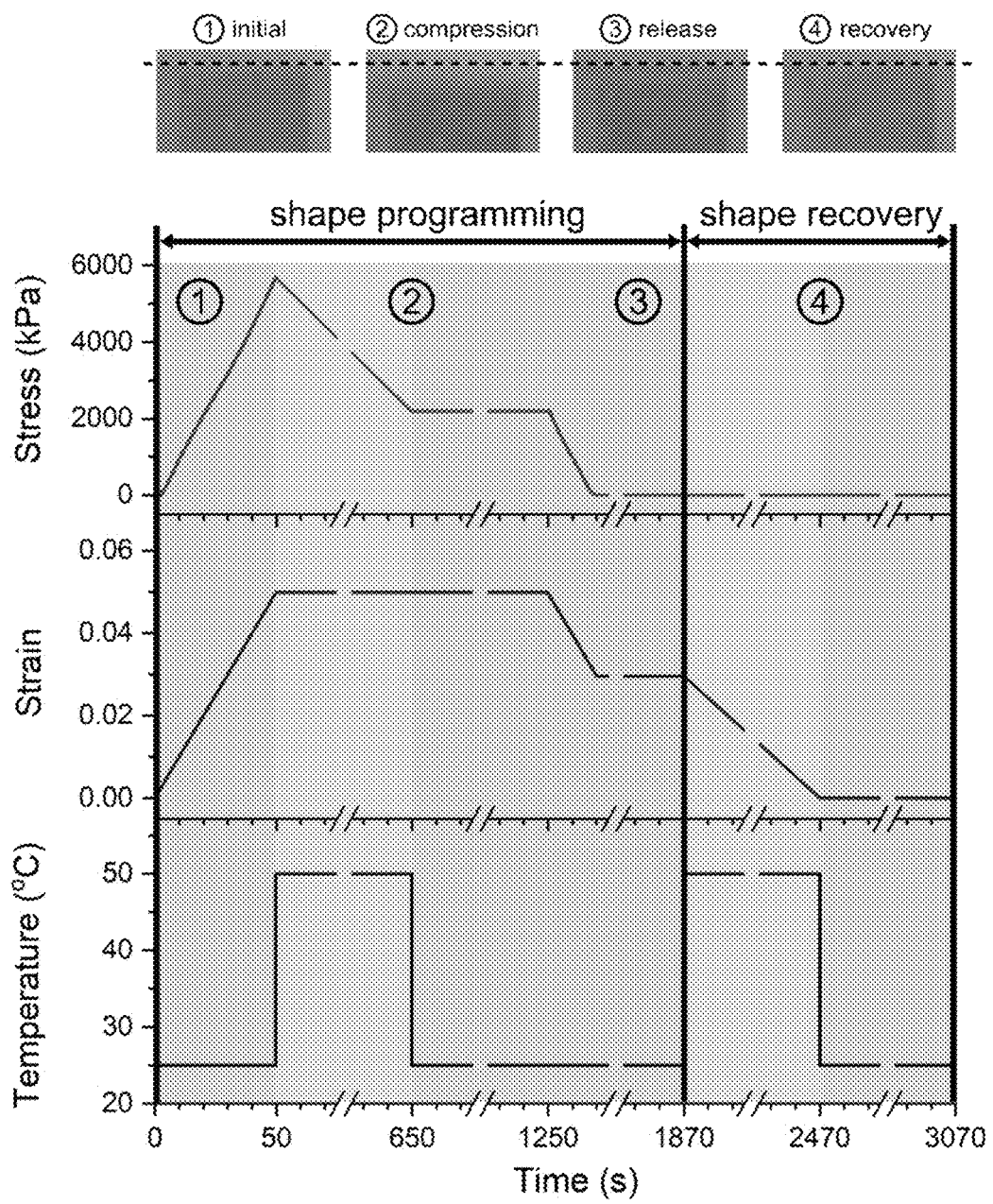
FIG. 6C is a graph of stress, strain, and temperature over time from a shape programming and shape recovery test of the SMP.

To demonstrate SME, shape programming and shape recovery of a 3D printed SMP beam was performed, the results of which are shown in FIG. 6C. Stress, strain and temperature during the process are plotted. The beam was compressed by 5% at 25° C. While maintaining the strain, the beam was heated to 50° C. and then cooled down to 25° C. again. Note that required stress to maintain the compressive strain reduced significantly due to fixing of deformed shape. After removal of mechanical loading, the deformed strain was retained at 3%. Even though only 60% of strain was fixed after release, it can be further improved using longer holding time and higher heating temperature. Upon heating back to 50° C., the original height of the beam was completely recovered.

Array Design

Figure 7A:
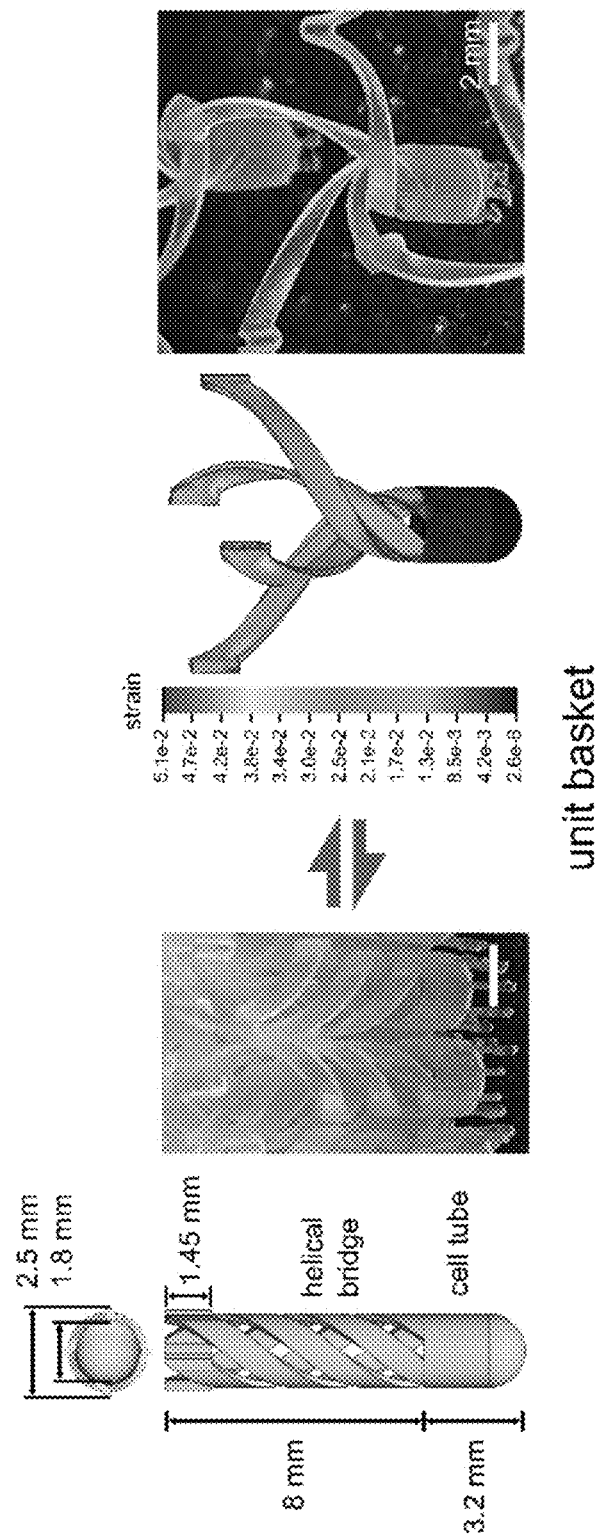
FIG. 7A illustrates an example of a prototype receptacle in contracted and extended states.

Arrays were designed as shown in FIGS. 5A-5C to meet dimensional requirements for transport between a 96-well plate and a histology cassette, as well as to satisfy stretchability and cell culture requirements. To fit 12×8 basket arrays in the histology cassette, a maximum dimension of one basket unit was restrained to 2.5 m×2.5 m×11.2 mm. As shown in FIG. 7A, the height of the cell tube was 3.2 mm and the height of the helical bridge was 8 mm. The opening of the cell tube was designed to be 1.8 mm in diameter to accommodate a 20 μL pipette tip used in cell seeding.

Wall thickness of cell tube and thickness of helical bridge were 200 μm. Width of helical bridge was 1.45 mm. Total length after full extension of helical bridge without considering constraint in local strain can be 22.1 mm. In the 96-well plate configuration, each basket was to be stretched to 9 m×9 mm. Height was approximately 10 mm due to unwinding of helical bridges. Results from a numerical simulation with proper constraints of a single unit basket revealed that local strain after stretching to the 96-well plate configuration was lower than 5.1%, which is half of the smallest measured failure strain from the experiments described with respect to FIG. 6B and which indicated that no breakage would occur during transformation. The receptacle and beam design and the resulting numerical analysis of the design are shown in FIG. 7A.

Figure 7B:
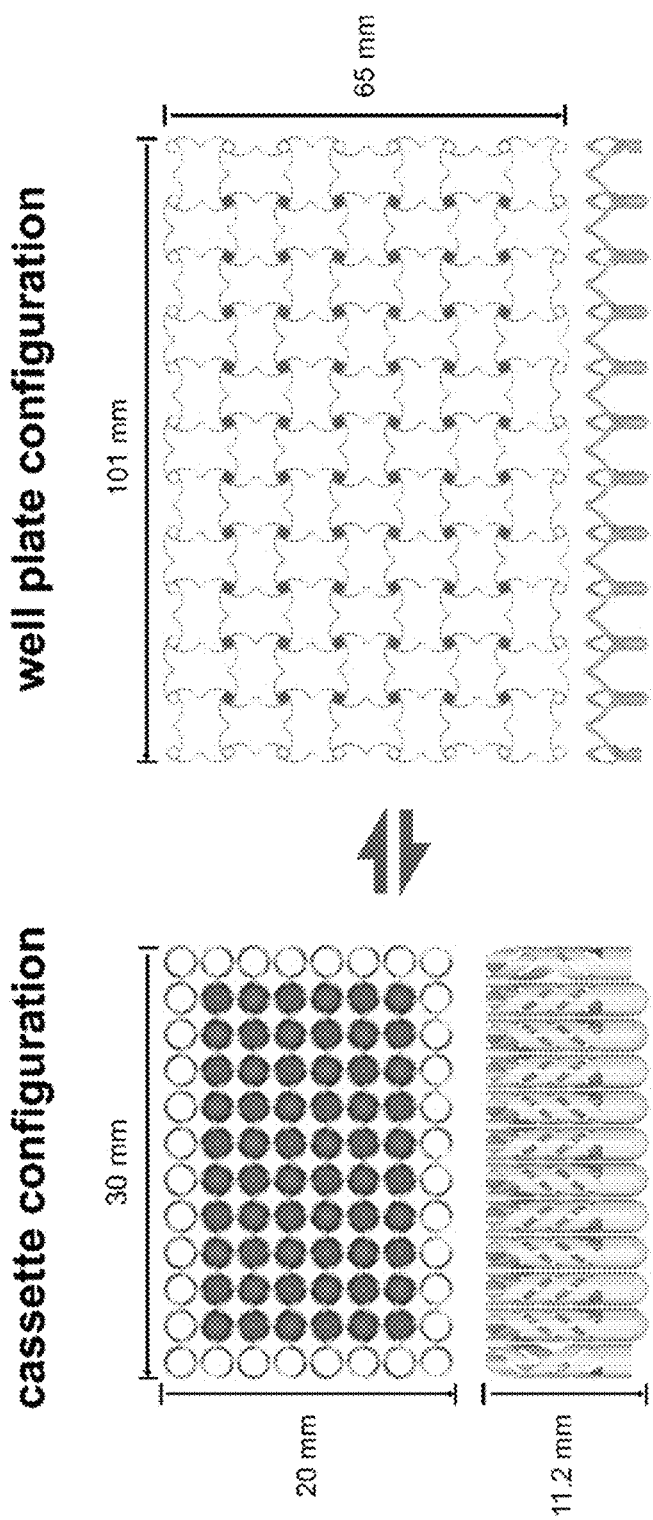
FIG. 7B illustrates schematic of a cassette configuration and a well plate configuration for an array of the prototype receptacles of FIG. 7A.

Cassette and well-plate configurations of the arrays are shown in FIG. 7B. Assembly of the basket arrays consisted of unit baskets having alternatively clockwise and counterclockwise helical bridges. Based on trials, such a configuration demonstrated less twisting of helical bridges during stretching than configurations that included only one rotational direction. In the cassette configuration, basket arrays were designed to have an overall dimension of 30 m×20 m×11.2 mm. In a stretched, well-plate configuration, the basket arrays were designed to have an overall dimension of 101 m×65 m×10 mm, as shown in FIG. 7B. Edge baskets were intentionally printed without bottoms for fixing onto a well plate during cell culturing (see Array Operation).

Figure 7C:
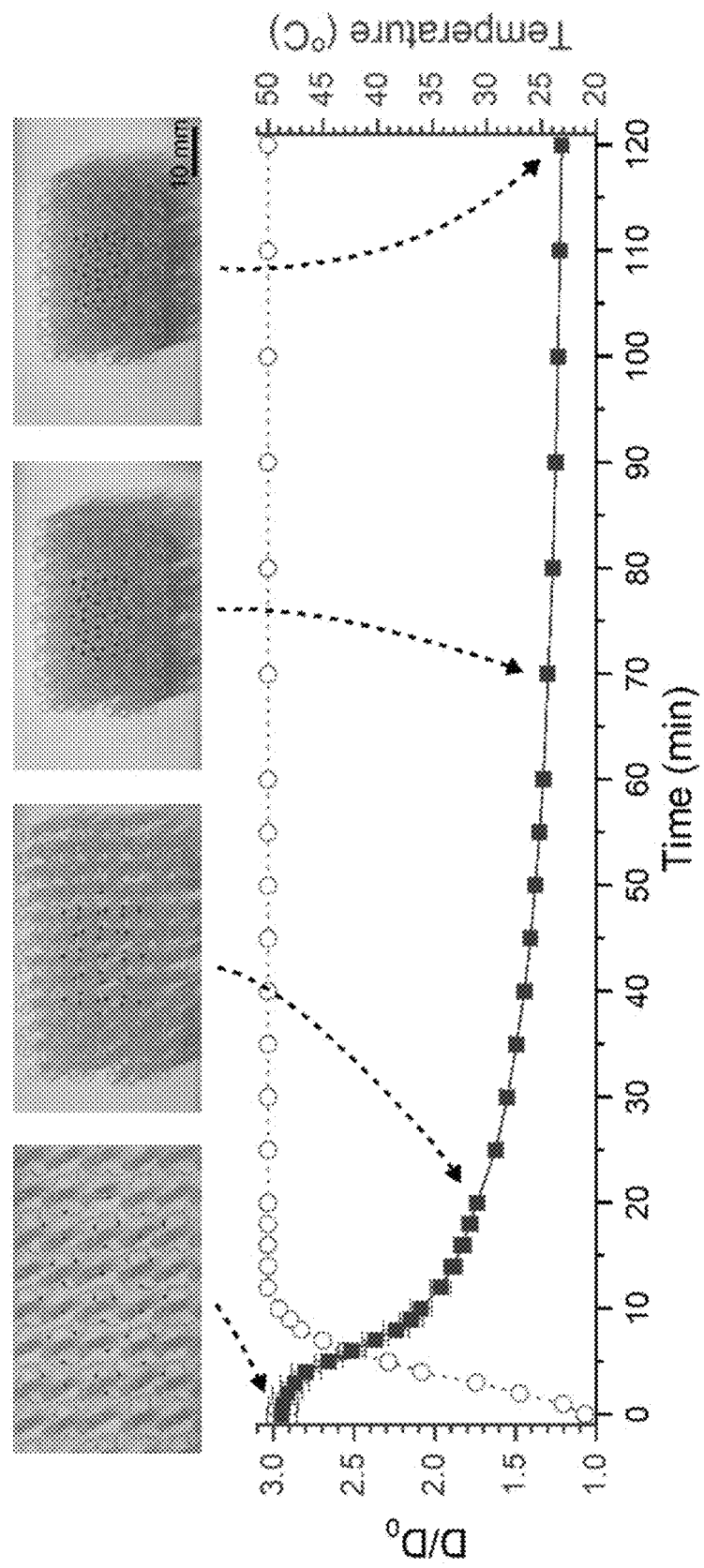
FIG. 7C illustrates ratio of original size of a prototype receptacle to a measured size of the receptacle over time during a heat recovery test of a prototype array according to FIG. 7B.

Results of heated recovery testing of the designed arrays are shown in FIG. 7C. Heated recovery was measured quantitatively using a customized digital image tracking code. Markers were labeled on the connecting points between bridges and were traced using digital image processing. $D_0$ indicates original size of a unit basket, which was 2.5 mm. D indicates measured size at timestamps during heating. Heating started from room temperature at 0 min for capturing size after shape fixing. Once the temperature reached 50° C., the temperature was maintained until the end of experiment. The starting ratio of $D_0/D$ at 0 min was 2.9 instead of 3.6 (ratio of size of well plate/size of cassette). This was caused by imperfect shape fixing of SMP during shape programming. After 120 min of heating, the basket arrays recovered to 1.2 times its original size instead of 1. This was due to friction between the bottom surface and basket arrays. From FIG. 7C, it can be seen that recovery mostly happened during the first 20 min of heating and slowed down significantly in the rest of experiment. A 10-min heating time was chosen in further cell-culturing operations as the temperature used for recovery was maintained at 50° C. (without heating from room temperature, as in this characterization experiment). Since basket arrays are flexible and can be squeezed to fit into cassettes after recovery, 100% recovery using long-time heating is not necessary and may be undesirable as cells may be negatively affected by exposure to the higher temperature of 50° C. than 37° C. for an extended period of time.

Figure 11A:
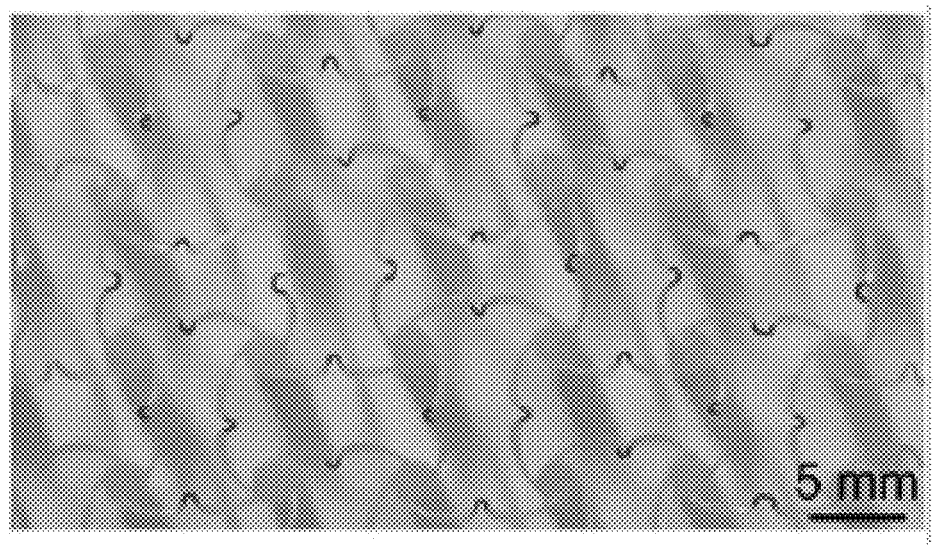
FIG. 11A depicts a prototype array in an expanded state with markers at bridge connections for shape recovery mapping.
Figure 11B:
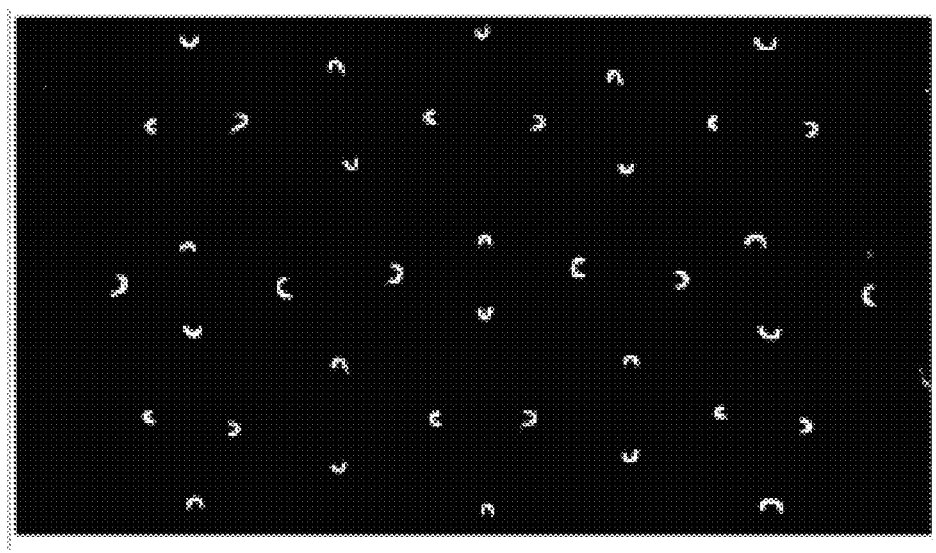
FIG. 11B depicts the photographed markers of the prototype array of FIG. 11A.
Figure 11C:
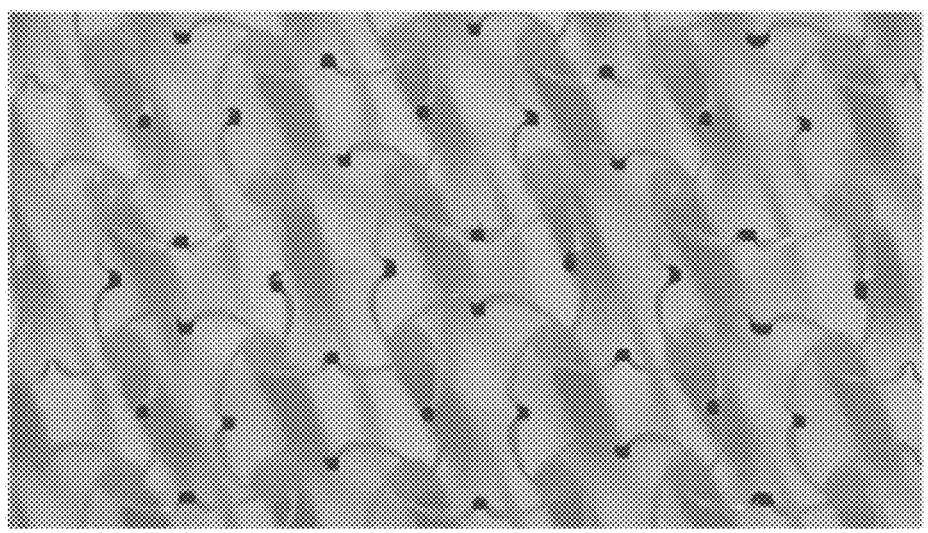
FIG. 11C depicts the detected markers of the prototype array of FIGS. 11A and 11B.

For shape recovery characterization, black markers were drawn on connecting parts of helical bridges, as shown in FIG. 11A. A 45-degree mirror was used on top of basket arrays so a digital camera (Canon 60D) can view the arrays from a horizontal configuration. The basket arrays and mirror were kept inside a temperature oven and the camera was maintained outside the oven. A transparent window at the door of oven was used for visibility during experiment. After obtaining video of shape recovery, an example of which is shown in FIG. 11B, image processing using MATLAB was applied on images at different timestamps to obtain coordinates of markers. Detected markers were indicated using red squares, as shown in FIG. 11C. Distance was then calculated to between corresponding markers to obtain size of baskets. Since there are clockwise (CW) and counterclockwise (CCW) baskets, periodicity in a basket arrays was considered to be a combination of one CW and one CCW basket. Six pairs of markers from a repeating unit (two baskets) were measured at each timestamp. Then results were divided by two to obtain average and standard deviation of size of one basket.

Array Operation

Operation of the arrays is shown in FIG. 8. At room temperature, a basket array in a cassette configuration was first mounted on a customized stretcher, as shown in FIGS. 9A-9D. The stretcher included eight rails configured to simultaneously move all carriages sitting in the rails between the dimension of a cassette and the dimension of a 96-well plate. To provide for uniform stretching, a number of rails is desired to be the same as the number of edge baskets. However, due to limited space at a cassette configuration, only eight rails were fit in the test device.

The top acrylic plate was laser cut with eight straight rails. Patterns of rails connected locations of eight evenly distributed baskets in the original configuration (17.5×27.5 mm) with locations of same baskets in the stretched configuration (105×165 mm) (stretching capability of 6 times). A bottom acrylic plate was laser cut with eight curved rails that are compatible with straight rails. Top rails had a width of 5 mm and bottom rails had a width of 3 mm. Cylindrical carriages had a diameter of 5 mm in top portion and 3 mm in bottom portion. Carriages with 12 needle pins (diameter of 0.8 mm) sitting in both rails can move from a small configuration to a large configuration by rotating the top plate against bottom plate.

Figure 9D:
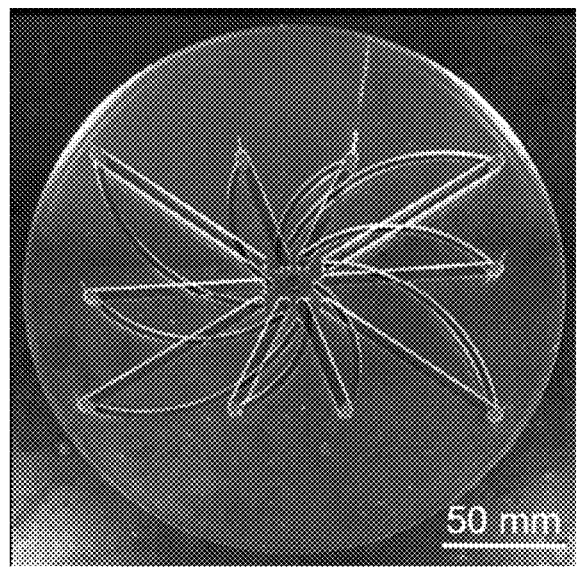
FIG. 9D depicts the example array and stretcher of FIG. 9C in the expanded configuration shown in FIG. 9B.

The basket array was stretched to a 96-well plate configuration by rotating the top and bottom plates against each other at room temperature. The helical bridges of each basket unwinded during rotation of the stretcher, as shown in FIGS. 9B and 9D. In the test device, in the compact configuration shown in FIGS. 9A and 9C, a first distance in the x-direction (A1) was 27.5 mm and a first distance in the y-direction (B1) was 17.5. After rotation, in the expanded configuration shown in FIGS. 9B and 9D, a second distance in the x-direction (A2) was 165 mm and a second distance in the y-direction (B2) was 105 mm.

After rotation, both the basket array and stretcher were placed in a temperature oven at 50° C. for 10 min and then cooled down to room temperature to fix the stretched shape. Then basket arrays were then removed from the stretcher with the temporarily programmed shape.

At this stage, the temporary shape did not match exactly with 96-well plate. Basket arrays were then mounted onto a fixture, a schematic of which is shown in FIGS. 10A-10B, by slightly further stretching of the edge baskets to match corresponding pins of the fixture. The fixture was designed to match edge units of basket arrays and a 96-well plate.

The fixture was 3D printed using a fused deposition modeling (FDM) printer (grint, Stratasys). The fixture included a window in its center and pins that match edge baskets with edge wells in 96-well plate. A CAD design of fixture the fixture is shown in FIGS. 10A-B. The dimensions of the fixture, with reference to FIG. 10A were as follows: 99 mm (A), 9 mm (B), 64 mm (C).

Another advantage of including a fixture is to restrain the SMPs recovery behavior over time. After fixing, a SMP will gradually restore its original shape at a temperature dependent speed (e.g., higher rate at higher temperature). Since cell culturing processes typically occur at a temperature of 37° C. for two weeks, a fixture can ensure that shape recovery of the array does not occur during this period of time.

The fixture with the basket array was then placed on a 96-well plate for cell seeding. Cells were injected into each basket using micropipette and cell culture media were added into wells and baskets. After cell culture, basket arrays were removed from the fixture and heated to 50° C. to induce shape recovery. Once the array reached a cassette configuration, it was ready for histology processing.

Example 2

Biocompatibility Verification of 4D Cell-Culture Arrays

Organoid growth in manufactured cell culture arrays was examined to verify biocompatibility of the arrays. In particular, 3D-printed cell-culture arrays were fabricated as described in Example 1 and used for histological analysis of patient derived organoids (PDOs) for glioblastoma (GBM) therapy.

The biocompatibility of the basket arrays for generating GBM spheres and GBM organoids and histological processing and imaging was examined.

Sphere and organoid numbers, viability, and differentiation potential were quantified upon basket memory reconfiguration at 50° C. Use of the cell-culture array was shown to reduce tissue fixation time from, historically, 1-3 days to 6 hours, as shown in the histological processing steps shown in FIG. 12A and obtained microtome sections shown in FIG. 12B. SMP baskets were also determined to be compatible with automated processing methods. Three rounds of histological processing and Hematoxylin and Eosin (H&E) staining determined the processing time and cutting parameters for use with the biomaterial, results of which are shown in FIG. 12B.

Figure 12A:
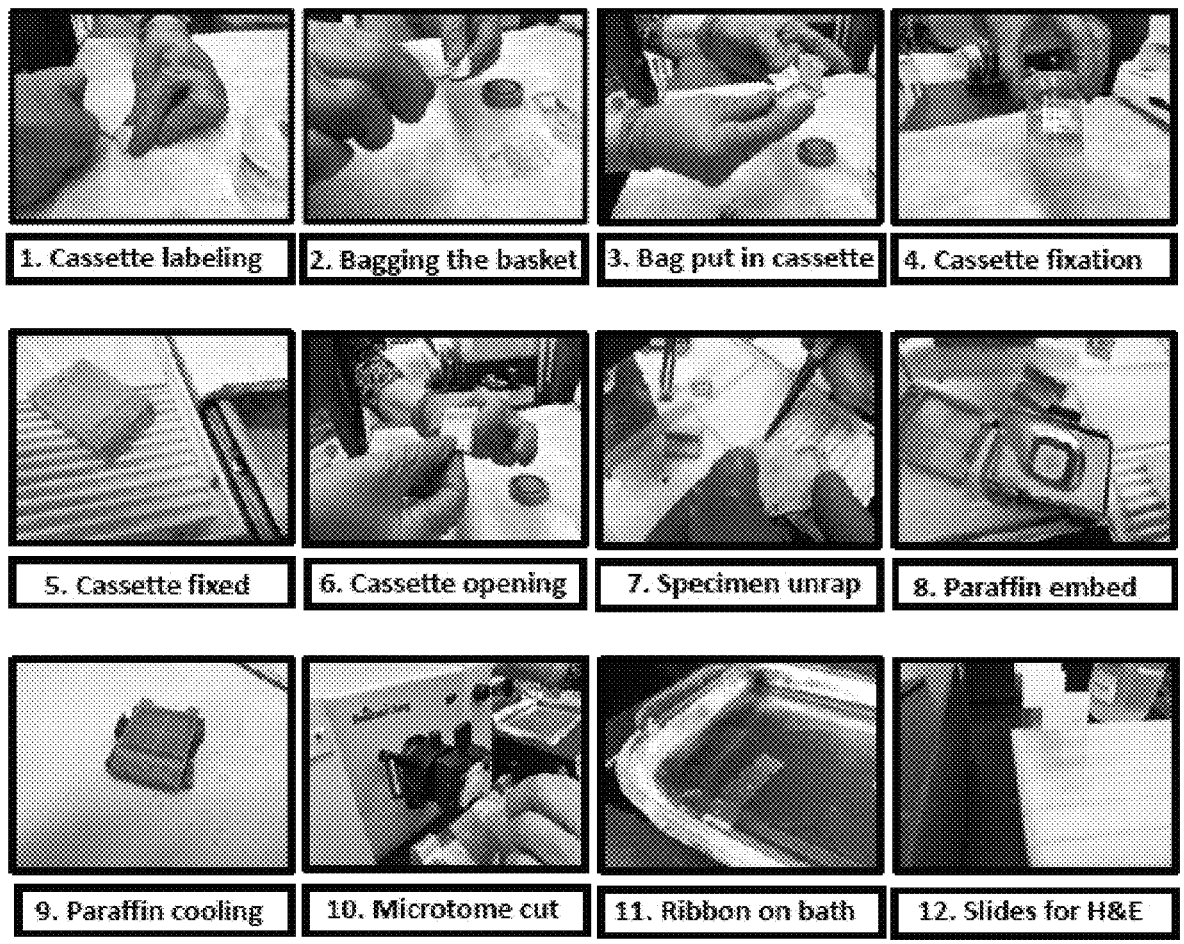
FIG. 12A illustrates a test process for histological processing with a prototype expandable array.
Figure 12B:
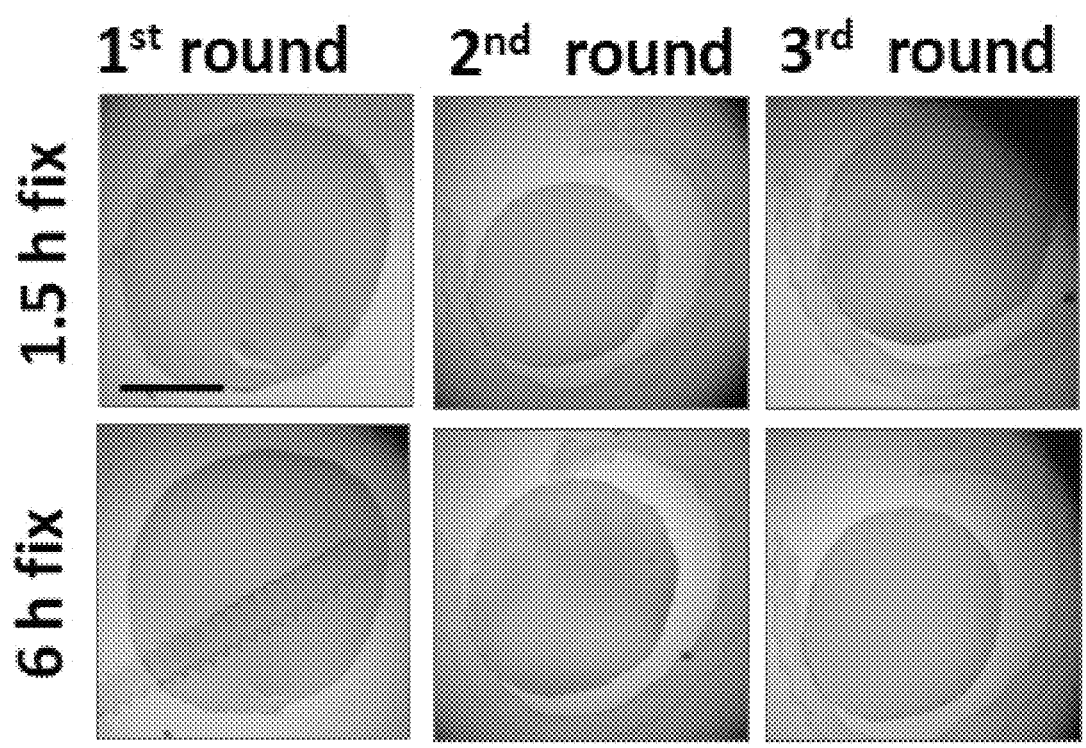
FIG. 12B illustrates Hematoxylin and Eosin (H&E) stained microtome sections obtained from the histological processing shown in FIG. 12A. The scale bar in 100 μm.
Figure 13:
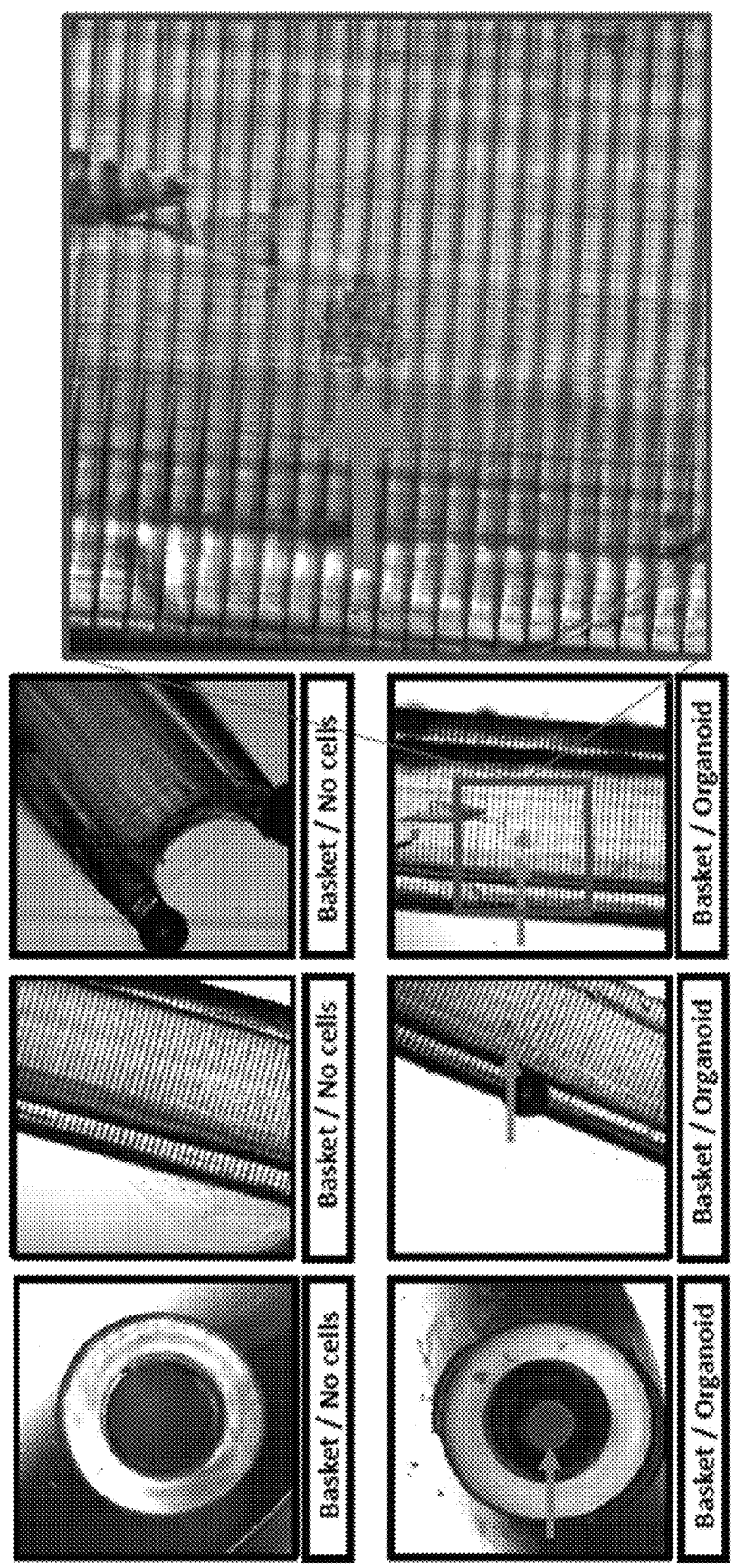
FIG. 13 depicts cross-section and side-section photos of prototype receptacles with and without cells.

SMP compatibility with 10% neutral buffered formalin fixation was supported, while GBM cell integrity was maintained in the twelve-step histological assay process shown in FIG. 12A. Individual baskets, intact or sectioned, were used to facilitate cell seeding and organoid formation, as shown in FIG. 13. Cross-section, side-section, and magnified areas of sample baskets without (top views) and with (bottom and right-side magnified views) cells plated as organoids are shown in FIG. 13. Note that the baskets allowed initiations of GBM PDOs within 72 hours, as shown in the magnified view in FIG. 13.

While SMP components were compatible, PEGDA 700 developed opacity with prolonged fixation and was replaced with PEGDA 250 in the prototype basket arrays.

Figure 14A:
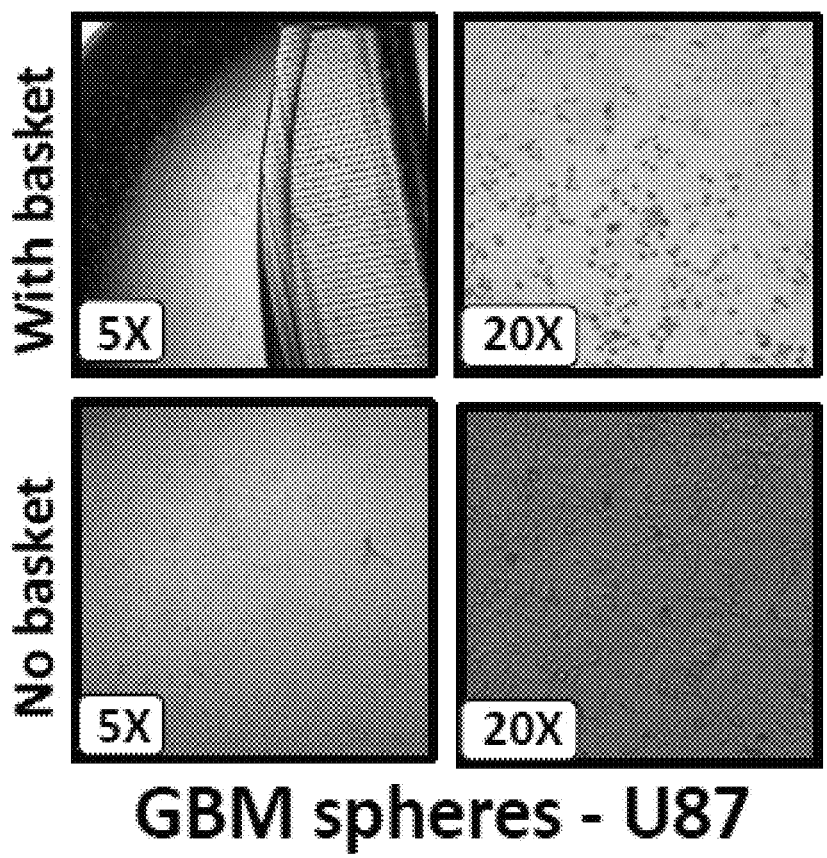
FIG. 14A depicts bright field images of glioblastoma (GBM) spheres derived from U87 cells in the presence of fetal bovine serum (FBS) and grown with and without receptacle arrays.

The effects of SMP components on cell viability were examined in both U87 and primary GBM 3D cultures. Formation of U87 GBM spheres within one week was overall comparable with or without SMP baskets, as shown in FIG. 14A. Bright field images of GBM spheres derived from U87 cells in the presence of FBS and grown with no basket and with baskets are shown in the bright field images of FIG. 14A.

Figure 14B:
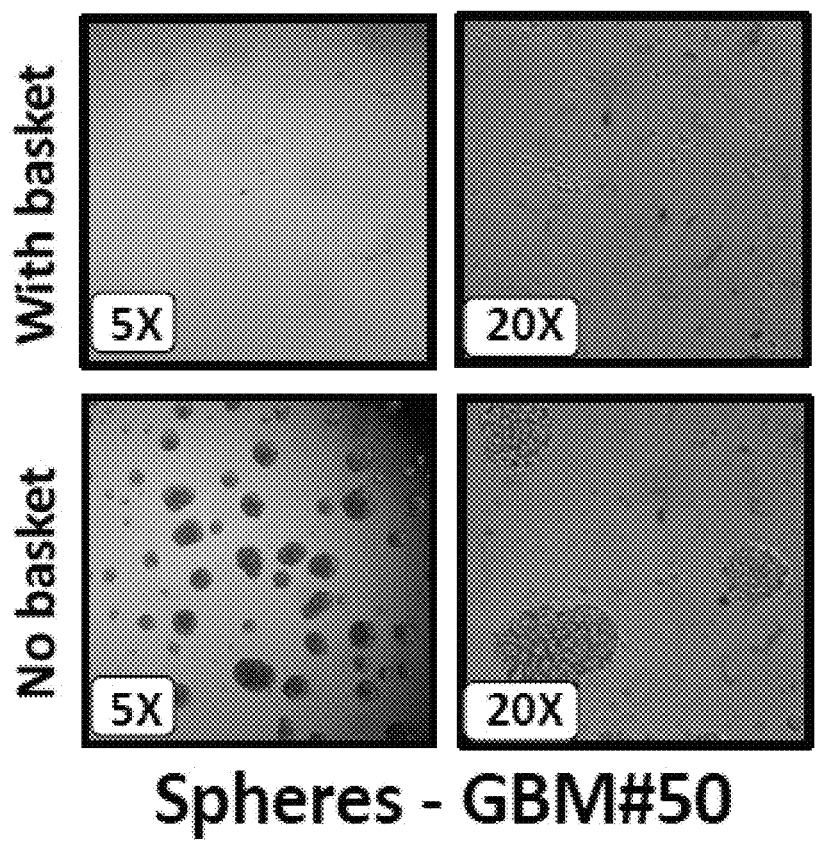
FIG. 14B depicts bright field images of GBM organoids grown in serum-free conditions with growth factors and derived from GBM #50 cells, grown with and without receptacle arrays.
Figure 14C:
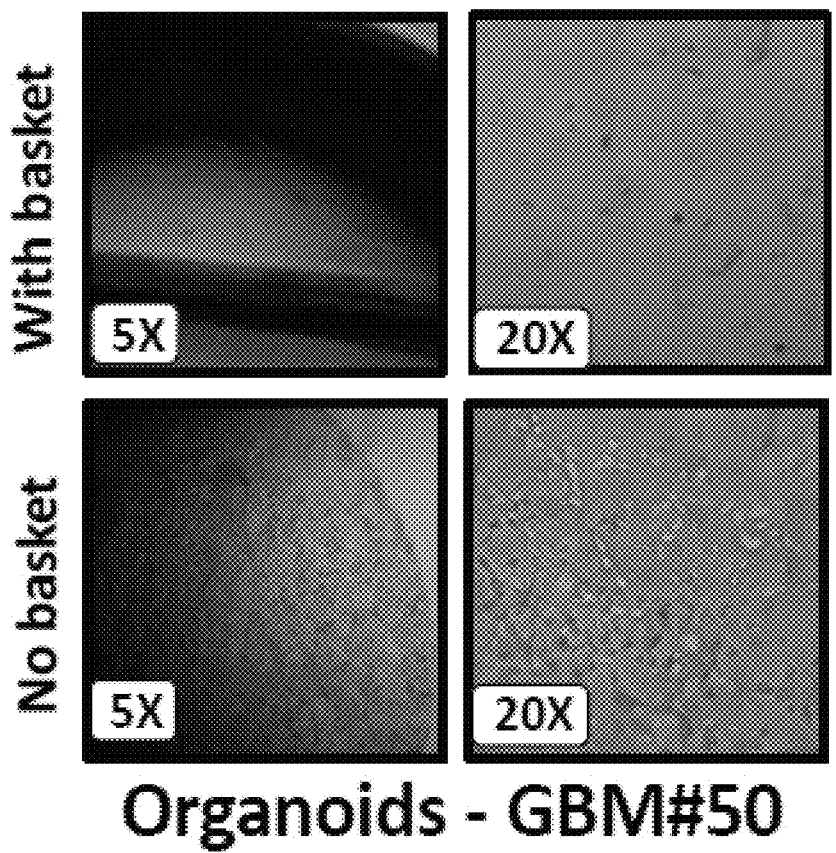
FIG. 14C depicts bright field images of GBM #50 cells grown in Matrigel spheres, grown with and without receptacle arrays.

When primary GBM#50 cells were grown in either serum-free sphere conditions (no matrigel) or as GBM organoids, large GBM spheres and diversified organoids with multicellular connections were detected after one or two weeks, respectively, in the absence of basket arrays. With the basket arrays, the number and size of primary spheres or organoids were significantly reduced (FIGS. 14B-C). GBM organoids grown in serum-free conditions with growth factors derived from GBM#50 cells with no basket and with baskets are shown in the bright field images of FIG. 14B. GBM #50 cells grown in matrigel spheres with no basket and with baskets are shown in the bright field images of FIG. 14C.

Unexpectedly, these studies suggested that serum or matrigel could have neutralizing effects on the biomaterial components. To investigate each component, it was first determined, by measuring media levels in prolonged cultures, that baskets were not absorbing media and, thus, were limiting growth factor availability. Notably, prolonged culture media were yellow-tinted and more alkaline compared to control culture, suggesting that the basket biomaterial could be leaching low levels of chemicals that may interfere with long-term organoid cultures.

SMP components, including poly (Ethylene glycol) diacrylate 250 (PEGDA 250), Bisphenol A (BPA), photo-initiator (PI) and photo-activator (PA) were each examined in the GBM intracellular ATP cell viability assay. Only PEGDA250, when used at three log concentration of median dose (1,000 fold in excess of EC50 at 7.2 µM) showed a significant loss of cell viability (FIGS. 15A-C), suggesting that low PEGDA 250 levels may be leaching from the basket during long-term organoid culture. Preincubation of the basket array after 3D printing into culture media, PBS, 10% BSA, or β-mercaptoethanol (at 10 µM or 50 µM) did not reverse the cell loss phenotype, but presoaking of basket arrays after 3D printing into 100% acetone, followed by PBS and ethanol washes did (FIGS. 16A-F). Based on these data, 3D printed SMP basket arrays were established for PDO generation and drug assays to identify effective treatments for primary GBM.

Figure 15A:
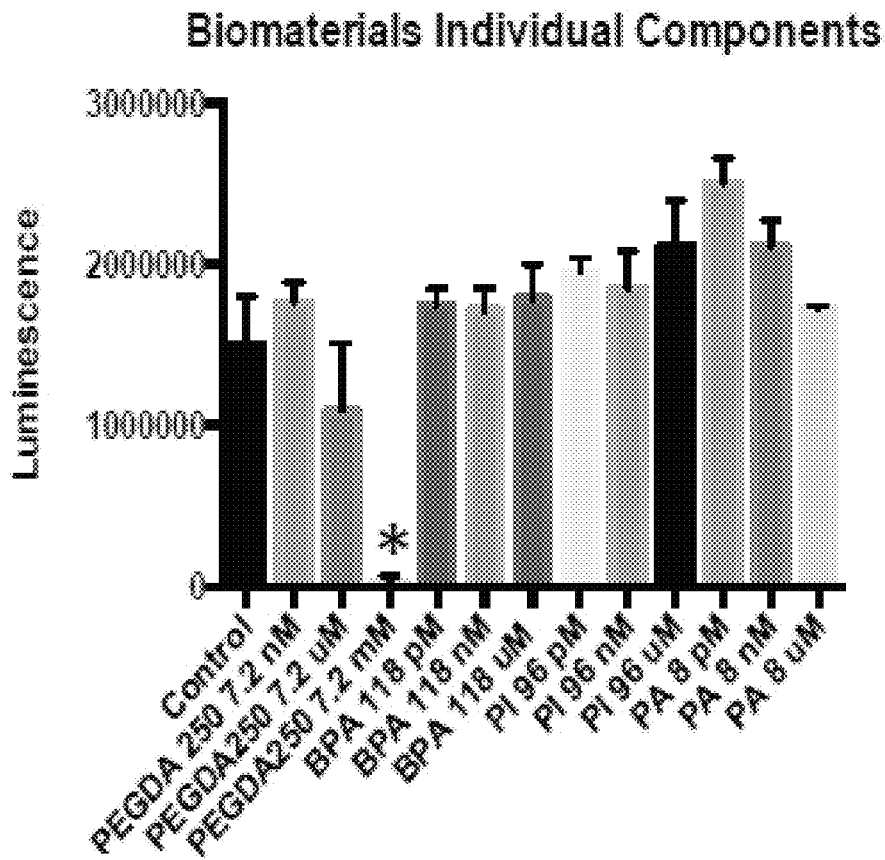
FIG. 15A is a graph of cell titer glo assay results versus component biomaterials for testing to determine GBM cell viability in receptacle arrays.
Figure 15B:
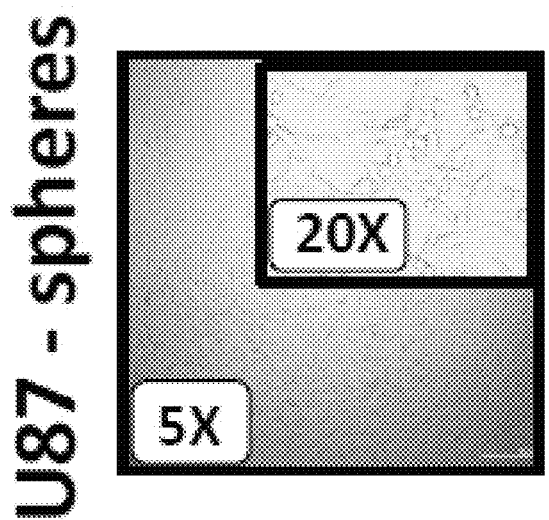
FIG. 15B is a low-power bright field image of control U87 spheres cultured for one week for the control of FIG. 15A, shown in 5× and 20× magnification.
Figure 15C:
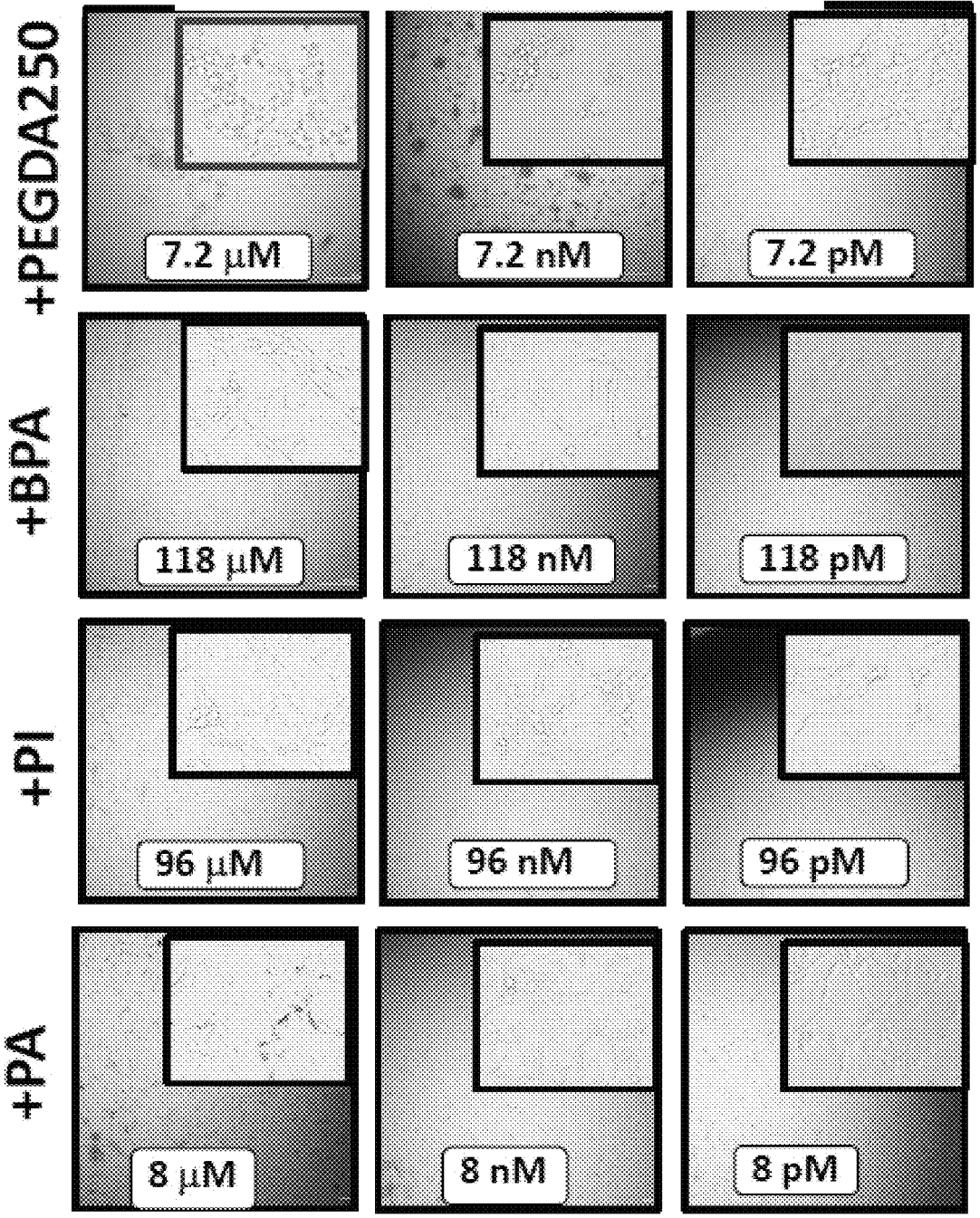
FIG. 15C depicts low-power bright field images of U87 spheres cultured for one week with the biomaterials of FIG. 15A, shown in 5× and 20× magnification.

FIG. 15A illustrates the results of the cell titer glo assay that utilizes ATP levels and was used to determine GBM viability in the presence of component biomaterials. FIGS. 15B and 15C are low-power images of bright fields of spheres cultured for one week in the presence of the indicated chemicals and concentrations. The insets are higher power (20×) magnification of the 5× images. Only PEGDA250 when used at 7.2 µM induced a significant loss of cell viability.

Figure 16A:
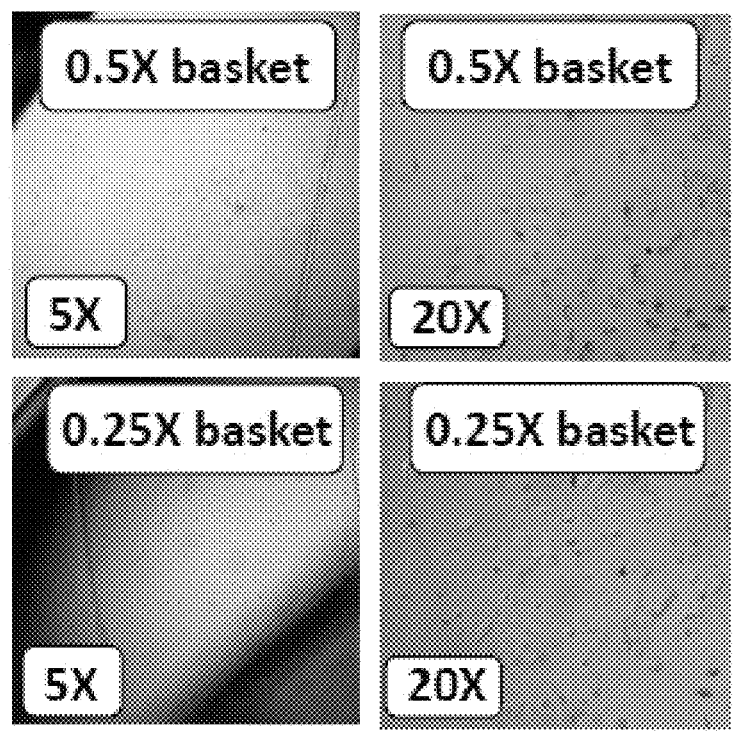
FIG. 16A depicts images of sphere cultures with cut baskets.
Figure 16B:
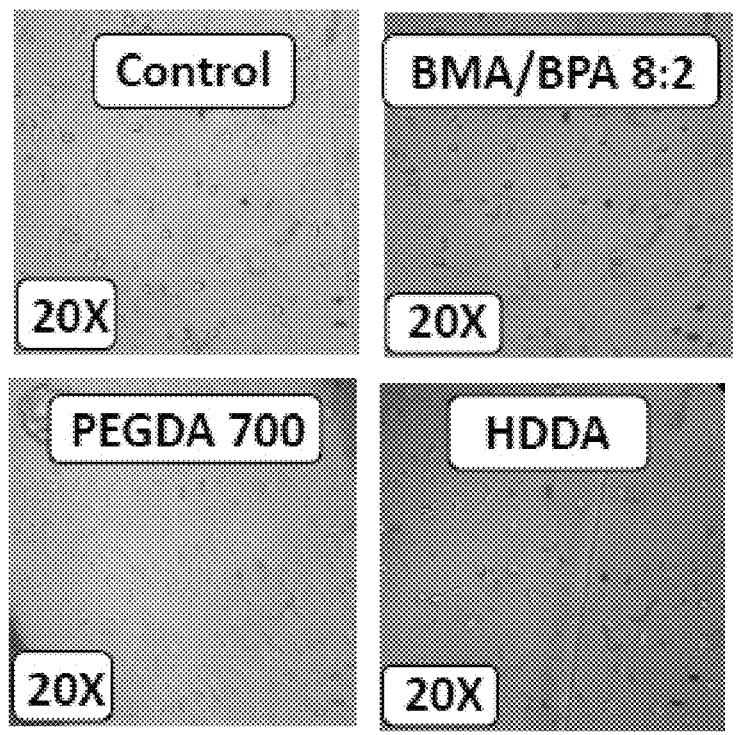
FIG. 16B depicts images of sphere cultures from samples of individually examined basket biomaterials.
Figure 16C:
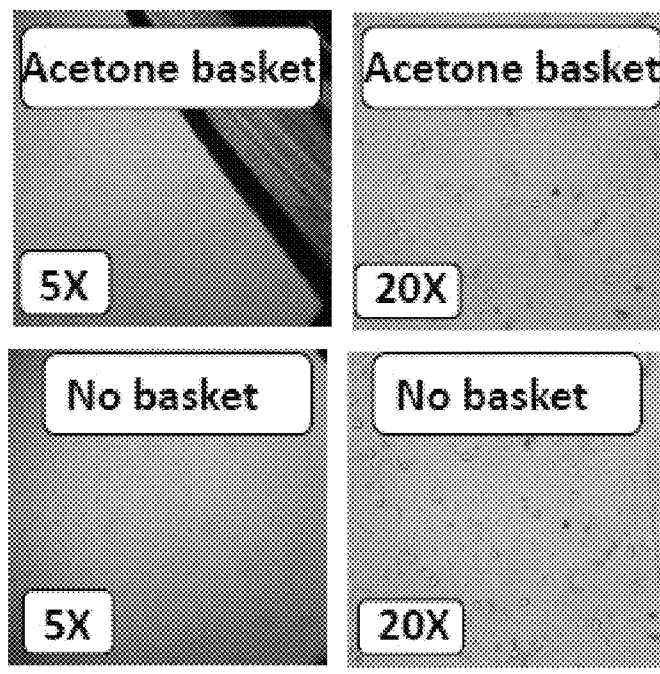
FIG. 16C depicts images of cell cultures without basket arrays and with basket arrays soaked in a 100% acetone bath after 3D printing.
Figure 16D:
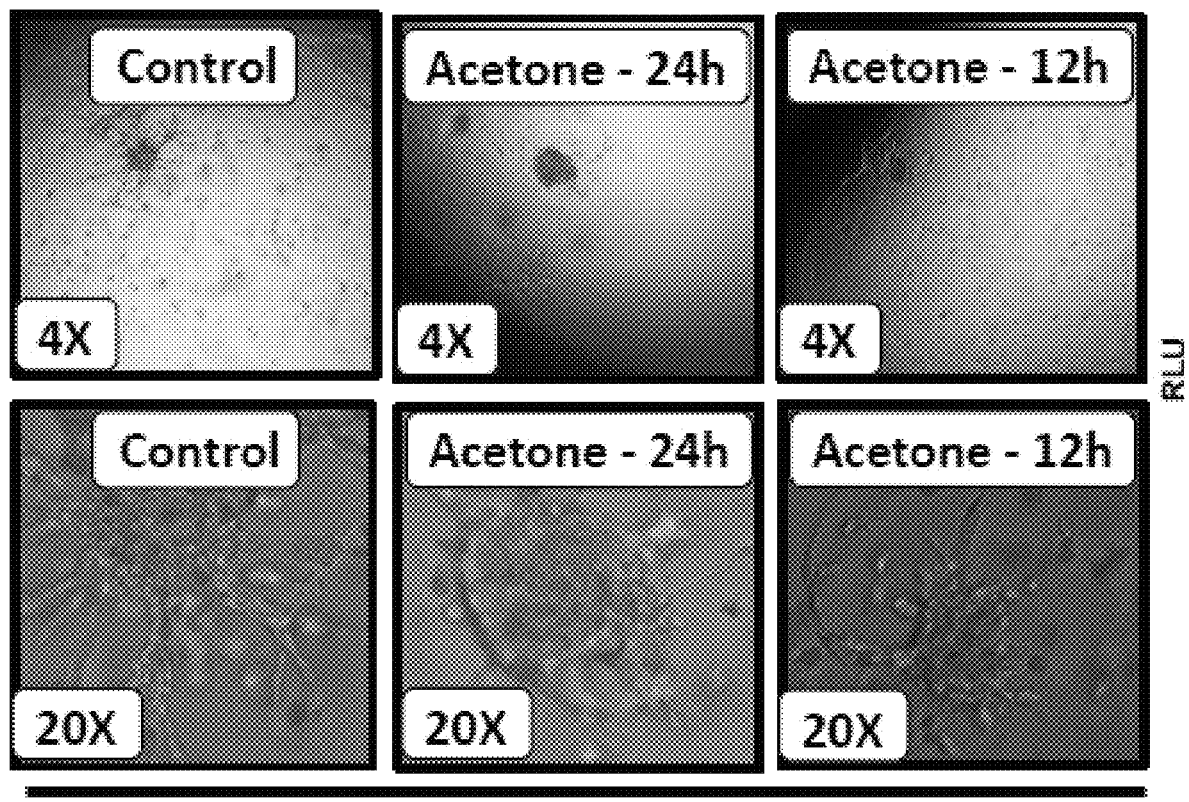
FIG. 16D depicts images of GBM organoid cultures without acetone soak and with 12 h and 24 h acetone soak.
Figure 16E:
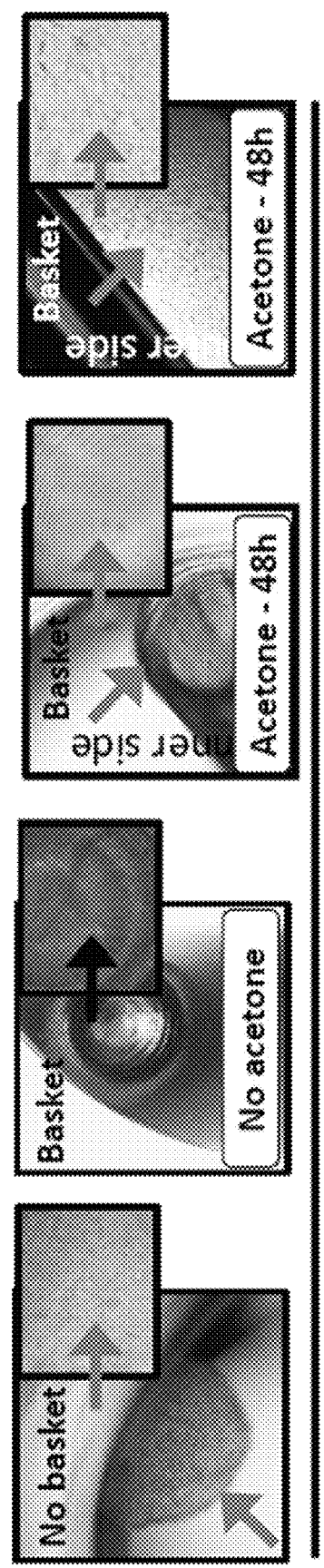
FIG. 16E depicts bright field images showing no GBM organoid grown in a basket when an acetone bath was not used and GBM organoid growth in a basket soaked in 100% acetone bath after 3D printing.
Figure 16F:
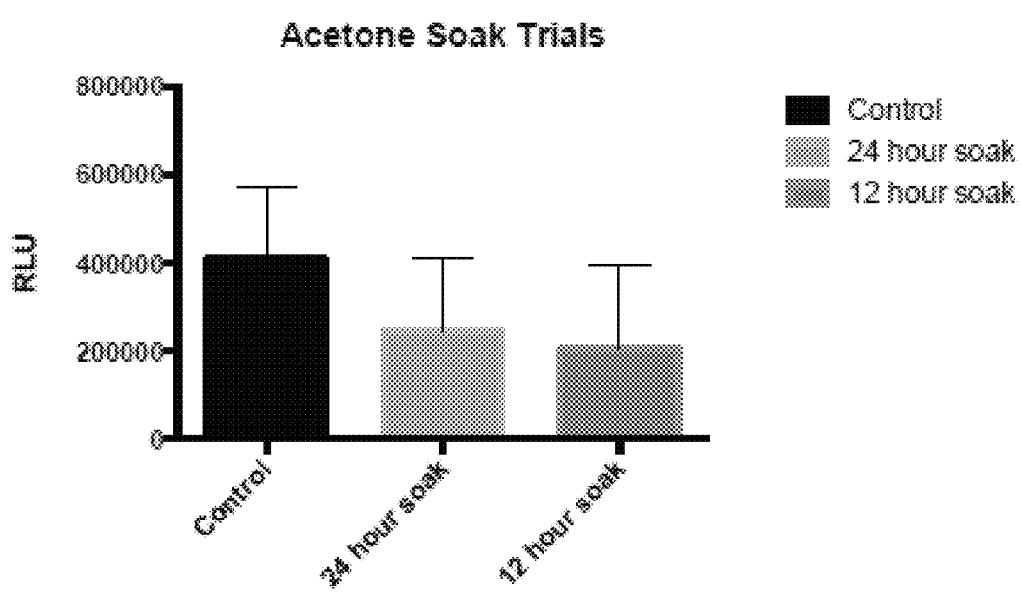
FIG. 16F is a graph of the results of the acetone soak trial depicted in FIG. 16D of Relative Light Units (RLU) versus control, 12 hour soak, and 24 hour soak.

Acetone soaking was shown to allow biomaterial basket GBM sphere and organoid long-term culture, as shown in FIGS. 16A-F. Different components of basket biomaterial were individually examined at the final concentrations used in the prototype basket array were shown to allow normal sphere culture (FIG. 16B). Soaking of a basket array in a 100% acetone bath after 3D printing allowed normal sphere culture (FIG. 16C). GBM organoid culture upon soaking for 12-14 h in acetone gradually improved effects (FIG. 16D and 16F). The soaking of a basket array in a 100% acetone bath after 3D printing allowed normal GBM organoid culture (FIG. 16E).

The platform developed was then examined with GBM tissues for both paraffin embedding for histological analysis and genomic sequencing, and with live GBM tissue for generating spheres and organoids for drug sensitivity testing. GBM tissues were subjected to exome sequencing to simultaneously detect the genetic alterations characteristic for adult GBM (GlioSeq) and identify deregulated pathways to guide the selection of targeted therapies. GlioSeq analyzes 30 genes for single nucleotide variants (SNVs) and indels, 24 genes for copy number variations (CNVs), and 14 types of structural alterations in BRAF, EGFR, and FGFR3 genes in a single workflow. Single cells were seeded at clonal densities in ultra-low attachment plates with basket arrays for sphere formation or in extracellular matrix droplets for organoid formation. GBM spheres or organoids were kept in serum-free growth factor supplemented conditions. The sphere assay is a functional assay to study GICs expressing stemness factors such as NESTIN, SOX2, OLIG2 and ZEB129. When bFGF and EGF were removed or GBM spheres cultured on polyornithine coated-surfaces, GBM cells underwent differentiation with GIC loss. In contrast, 3D cultured GBM organoids were heterogenous and capable of interconnecting (mimicking brain cells) and differentiating into cells with multiple cell phenotypes. Immunofluorescence (IF) for the neural stem cell protein NESTIN, and primitive neuroepithelium neuron-specific TUBULIN-beta-III and mature astrocytic Glial fibrillary acidic protein allowed to distinguish stemness from differentiation.

The basket arrays were used to deploy rapid single cell derived sphere and organoid assays to assess tumor cell viability, tumor invasion, terminal differentiation and resistance to therapy for cancer drug discovery and drug validation. Single and/or clonal GBM cell derived PDOs formed in 2 weeks and demonstrated invasion of the semisolid matrix by extended invadopodia. PDOs were treated for 72-hours with standard chemotherapy (TMZ) and/or molecularly targeted agents, targeting mTOR, PI3K, BMI1, EGFR, and DDR, among others. Following treatments, the entire 4D printed basket arrays were evolved, with a 10-min heating step at 50° C., to their programmable cassette size to directly perform histological and IHC validation on the same day, and with the convenience of maintaining the same tissue plate arrangement. The concentrations inhibiting viability by 50% (GI50), real time activated caspase 3 for detection of apoptotic cells and GBM tumor cell invasion in live intact organoid cells were less impacted by standard TMZ than targeted therapies. Critically, treatment with molecularly targeted agents alone or in combination had significantly more GBM organoid cell killing than TMZ, particularly in apparently TMZ resistant organoids, with targeted therapy reducing EGFR expression in organoid cells that were not affected by TMZ treatment, and with effective biomarker responses to targeted therapies, even at lower level combinations.

The cell-culture array platform allowed the entire patient tissue and drug response assessment to be completed in <20 days. When including exome and/or single cell sequencing, histological, IHC and targeted therapeutic assays, the array platform was demonstrated to offer dynamic, automated and quantitative drug analyses, thus allowing the discovery of novel preclinical therapeutic approaches that can be assessed in clinical trials and may be used to examine and select personalized therapies in precision medicine oncology.

While example embodiments have been particularly shown and described, it will be understood by those skilled in the art that various changes in form and details may be made therein without departing from the scope of the embodiments encompassed by the appended claims.

REFERENCES

1. Giannitelli S M, Mozetic P, Trombetta M, Rainer A. Combined additive manufacturing approaches in tissue engineering. 2015, Acta Biomater 24:1-11.

2. Truby R L, Lewis J A. Printing soft matter in three dimensions. 2016, Nature 540:371-378.

3. Chan V, Jeong J H, Bajaj P, Collens M, Saif T, Kong H, Bashir R. Multi-material bio-fabrication of hydrogel cantilevers and actuators with stereolithography. 2012, Lab Chip 12:88-98.

4. Tumbleston J R, Shirvanyants D, Ermoshkin N, Janusziewicz R, Johnson A R, Kelly D, Chen K, Pinschmidt R, Rolland J P, Ermoshkin A, Samulski E T, DeSimone J M. Additive manufacturing. Continuous liquid interface production of 3D objects. 2015, Science 347:1349-52.

5. Zheng X, Deotte J, Alonso M P, Farquar G R, Weisgraber T H, Gemberling S, Lee H, Fang N, Spadaccini C M. Design and optimization of a light-emitting diode projection micro-stereolithography three-dimensional manufacturing system. 2012, Rev Sci Instrum 83:125001.

6. Gladman A S, Matsumoto E A, Nuzzo R G, Mahadevan L, Lewis J A. Biomimetic 4D printing. 2016, Nat Mater 15:413-8.

7. Raviv D, Zhao W, McKnelly C, Papadopoulou A, Kadambi A, Shi B, Hirsch S, Dikovsky D, Zyracki M, Olguin C, Raskar R, Tibbits S. Active printed materials for complex self-evolving deformations. 2014, Sci Rep 4:7422. PMC4270353.

8. Mao Y, Yu K, Isakov M S, Wu J, Dunn M L, Jerry Qi H. Sequential Self-Folding Structures by 3D Printed Digital Shape Memory Polymers. 2015, Sci Rep 5:13616. PMC4562068.

9. Couchman, P. R. Compositional Variation of Glass Transition Temperatures. 2. Application of the Thermodynamic Theory to Compatible Polymer Blends. Macromolecules 11, 1156-1161, doi: 10.1021/ma60066a018 (1978).

The teachings of all patents, published applications and references cited herein are incorporated by reference in their entirety.

What is claimed is:

1. A kit comprising:
    an expandable array comprising:
        a plurality of receptacles configured to receive a biological sample, and
        a plurality of beams, each beam of the plurality of beams disposed to extend between and connect at least two receptacles, the plurality of beams comprising a a programmable material configured to transition each beam from an expanded state to a contracted state upon application of a stimulus;
    one or more biomolecules; and
    cell culture medium or ingredients for making a cell culture medium.

2. An expandable array, comprising:
    a plurality of receptacles configured to receive a biological sample; and
    a plurality of beams, each beam of the plurality of beams disposed to extend between and connect at least two receptacles, the plurality of beams comprising a programmable material configured to transition each beam from an expanded state to a contracted state upon application of a stimulus.

3. The expandable array of claim 2, wherein the programmable material is a magnetoactive material and the stimulus is a magnetic field.

4. The expandable array of claim 3, wherein the magnetoactive material comprises a polymer material within which magnetic or magnetizable particles are disposed.

5. The expandable array of claim 4, wherein the magnetic or magnetizable particles comprise neodymium iron boron.

6. The expandable array of claim 4, wherein the polymer is an elastomer.

7. The expandable array of claim 3, wherein each beam of the plurality of beams comprises at least two sections of magnetoactive material having opposite magnetic orientation.

8. The expandable array of claim 7, wherein each beam is configured to fold at a transition between the at least two sections.

9. The expandable array of claim 2, wherein at least a subset of the plurality of beams are disposed to extend from a top edge of a respective receptacle.

10. The expandable array of claim 2, wherein, in the expanded state, each beam of the plurality of beams extends horizontally between connected receptacles.

11. The expandable array of claim 2, wherein, in the contracted state, each beam of the plurality of beams is folded vertically between connected receptacles.

12. The expandable array of claim 2, wherein the array has a width of about 20 mm to about 30 mm and a length of about 25 mm to about 35 mm when each beam is in the contracted state.

13. The expandable array of claim 2, further comprising a handle located at a perimeter of the array.

14. The expandable array of claim 2, wherein each receptacle of the plurality of receptacles comprises a mesh structure.

15. The expandable array of claim 14, wherein the mesh structure comprises a pore size of about 2 µm to about 10 µm.

16. The expandable array of claim 2, wherein the plurality of receptacles is arranged in an 8×12 array.

17. The expandable array of claim 2, wherein the plurality of receptacles is arranged in a 4×6 array.

18. A method of maintaining a biological sample, comprising:
    placing an expandable array comprising a plurality of receptacles and a plurality of beams in a multiwell plate, each beam of the plurality of beams disposed to extend between and connect at least two receptacles and comprising a programmable material configured to transition each beam from an expanded state to a contracted state upon application of a stimulus;
    placing a biological sample within at least a subset of the plurality of receptacles;
    removing the expandable array containing the biological sample from the multiwell plate;
    exposing the expandable array to the stimulus, the plurality of beams responsively transitioning to a contracted state, the biological sample being maintained within the array during transition.

19. The method of claim 18, wherein exposing the expandable array to a stimulus includes exposing the array to a magnetic field.

20. The method of claim 18, further comprising transferring the expandable array containing the biological sample to a histology cassette.

21. The method of claim 20, wherein a relative configuration of the receptacles is maintained during transfer of the expandable array from the multiwell plate to the histology cassette.

22. The method of claim 20, wherein the biological sample is maintained within the receptacles during transfer of the expandable array from the multiwell plate to the histology cassette.

23. The expandable array of claim 2, wherein the programmable material is a shape-memory polymer.

24. The method of claim 18, wherein exposing the expandable array to a stimulus includes exposing the array to a temperature change.

* * * * *